(12) United States Patent
Balle-Petersen et al.

(10) Patent No.: US 6,383,177 B1
(45) Date of Patent: May 7, 2002

(54) APPARATUS FOR TISSUE TREATMENT

(75) Inventors: Olav Balle-Petersen, Humlebaek; Bjarne Asah, Taastrup; Casper Dolleris, Frederiksberg, all of (DK)

(73) Assignee: Asah Medico A/S, Hvidovre (DK)

(*) Notice: Subject to any disclaimer, the term of this patent is extended or adjusted under 35 U.S.C. 154(b) by 0 days.

(21) Appl. No.: 09/459,540

(22) Filed: Dec. 13, 1999

Related U.S. Application Data

(63) Continuation-in-part of application No. PCT/DK98/00372, filed on Aug. 28, 1998, and a continuation-in-part of application No. 08/974,429, filed on Nov. 19, 1997, now Pat. No. 6,074,382.

(30) Foreign Application Priority Data

Aug. 29, 1997 (DK) .................................................. 0989/97

(51) Int. Cl.[7] .............................................. A61B 18/18
(52) U.S. Cl. .............................. 606/9; 606/10; 606/11; 606/12; 607/89
(58) Field of Search .............................. 606/2, 3, 9–13, 606/14–17; 607/89

(56) References Cited

U.S. PATENT DOCUMENTS

| | | | |
|---|---|---|---|
| 3,307,553 A | | 3/1967 | Liebner |
| 3,821,510 A | | 6/1974 | Muncheryan |
| 4,140,130 A | | 2/1979 | Storm, III |
| 4,913,132 A | | 4/1990 | Gabriel |
| 5,057,104 A | * | 10/1991 | Chess .......................... 606/9 |
| 5,282,797 A | | 2/1994 | Chess |
| 5,330,519 A | | 7/1994 | Mason et al. |
| 5,344,418 A | | 9/1994 | Ghaffari |
| 5,405,368 A | | 4/1995 | Eckhouse |
| 5,456,260 A | | 10/1995 | Kollias et al. |
| 5,474,549 A | | 12/1995 | Ortiz et al. |
| 5,486,172 A | | 1/1996 | Chess |

(List continued on next page.)

FOREIGN PATENT DOCUMENTS

| | | |
|---|---|---|
| DE | A13-837248 | 5/1990 |
| DE | 198529848 | 5/2000 |
| EP | A20-763371 | 3/1997 |
| EP | A20-783904 | 7/1997 |
| EP | A01-788765 | 8/1997 |
| EP | A10788765 | 8/1997 |
| EP | A20827716 | 3/1998 |
| EP | A10880941 | 12/1998 |
| EP | B10699038 | 3/1999 |
| EP | A20933096 | 8/1999 |
| WO | 8606527 | 11/1986 |
| WO | 9308877 | 5/1993 |
| WO | 9400194 | 1/1994 |
| WO | 9503089 | 2/1995 |
| WO | 9625979 | 8/1996 |
| WO | 9824514 | 6/1998 |
| WO | 9825528 | 6/1998 |
| WO | 9833558 | 8/1998 |
| WO | 9846133 | 10/1998 |
| WO | 9851235 | 11/1998 |
| WO | 9855180 | 12/1998 |
| WO | 9857588 | 12/1998 |
| WO | 9917668 | 4/1999 |
| WO | 9946005 | 9/1999 |

*Primary Examiner*—Roy Gibson
(74) *Attorney, Agent, or Firm*—Birch, Stewart, Kolasch & Birch, LLP

(57) ABSTRACT

An apparatus for cosmetic tissue treatment having a light emitter for emission of a light beam. The light beam is directed towards a target area to be treated, and a detector detects tissue parameters in the target area. A light beam control controls at least one parameter of the first light beam in response to the detected at least one tissue parameters. The tissue parameters can include texture, elasticity, size, and shape. The apparatus may be used for ablating a thin epidermal layer of the derma of a patient and also marks on the tissue such as marks from chloasma, liver spots, red spots, tattoos, blood vessels just below the surface, etc., as well as warts, wounds, hair follicles, etc., may be ablated or treated.

32 Claims, 14 Drawing Sheets

U.S. PATENT DOCUMENTS

| | | |
|---|---|---|
| 5,531,740 A | 7/1996 | Black |
| 5,588,428 A | 12/1996 | Smith et al. |
| 5,595,568 A * | 1/1997 | Anderson et al. ............... 606/9 |
| 5,620,478 A | 4/1997 | Eckhouse |
| 5,628,744 A * | 5/1997 | Coleman et al. ............... 606/12 |
| 5,630,811 A | 5/1997 | Miller |
| 5,653,706 A | 8/1997 | Zavislan et al. |
| 5,735,276 A | 4/1998 | Lemelson |
| 5,742,392 A | 4/1998 | Anderson et al. |
| 5,743,902 A | 4/1998 | Trost |
| 5,779,702 A | 7/1998 | Fard |
| 5,810,801 A | 9/1998 | Anderson et al. |
| 5,814,040 A | 9/1998 | Nelson et al. |
| 5,820,626 A | 10/1998 | Baumgardner |
| 5,830,208 A | 11/1998 | Muller |
| 5,836,939 A | 11/1998 | Negus et al. |
| 5,851,181 A | 12/1998 | Talmor |
| 5,853,407 A | 12/1998 | Miller |
| 5,860,968 A | 1/1999 | Wojcik et al. |
| 5,865,828 A | 2/1999 | Jeng |
| 5,868,731 A | 2/1999 | Budnik et al. |
| 5,868,732 A | 2/1999 | Waldman et al. |
| 5,957,915 A | 9/1999 | Trost |
| 6,096,029 A * | 8/2000 | O'Donnell, Jr. ............... 606/9 |
| 6,162,211 A * | 12/2000 | Tankovich et al. ............. 606/9 |

\* cited by examiner

APPARATUS FOR TISSUE TREATMENT

This is a Continuation-In-Part of Application No. 08/974,429, filed Nov. 19, 1997, now U.S. Pat. No. 6,074,382 and PCT International Application No. PCT/DK98/00372, which has an international filing date of Aug. 28, 1998, the entire contents of both files being herein incorporated by reference.

FIELD OF THE INVENTION

The present invention relates to an apparatus for tissue treatment, such as cosmetic tissue treatment.

BACKGROUND OF THE INVENTION

It is known to utilise laser light for tissue treatment, such as cosmetic tissue treatment, removal of hair, photocoagulation of veins, etc.

During cosmetic tissue treatment, a laser ablates a thin epidermal layer of illuminated derma of a patient. During healing, a new epidermal layer is formed on the ablated surface having the look of the derma of a young person, i.e. the new epidermal layer is formed without previously existing scars, wrinkles, etc.

Lasers that operate at a wavelength that is absorbed in water are used for cosmetic tissue treatment. When the laser power density ($W/mm^2$) at illuminated cells is sufficient, cellular water is superheated causing small explosions that disrupt heated cells.

During removal of an epidermal layer, it is essential not to damage underlying or surrounding tissue. Residual heat may cause non-ablated cells to char and become necrotic, whereby new scars may be formed and thus, it is desirable to apply laser power for a short time, to minimize transmission of conducted heat to underlying and surrounding tissue.

It is therefore desired to accurately control the amount of light energy transferred to derma to be ablated. The amount of energy must be sufficient for the dermal cells to vaporize and, simultaneously, the amount of residual energy heating non-ablated cells must be so low that non-ablated cells will not be damaged.

Apparatuses for cosmetic tissue treatment are known, comprising a $CO_2$ laser emitting a laser beam and a laser articulating arm with mirrors for reflection of the laser beam, so that the laser beam is transmitted inside the articulating arm. Further, the arm has a number of joints, so that the arm can be moved around by an operator. A handpiece to be held by the operator is connected to the arm. The laser beam is moved or scanned across a target surface by adjustable mirrors connected to motors and mounted in the arm. The scan pattern of the laser beam is an archimedes spiral. The laser spot formed by the laser beam on the target surface moves along the spiral at a constant angular speed.

It is a disadvantage of the known apparatus that the energy density delivered to the target surface is non-uniform across the scanned surface area of the spiral, as more energy is delivered at the centre of the spiral than at the circumferential of the spiral.

It is another disadvantage of the known apparatus that the circular outline of the scan pattern leads to non-uniform scanning of an area that is larger than the area of the scan spiral as either 1) areas that have not been scanned will remain on the surface, when abutting spirals or 2) ablated areas will be scanned more than once, due to overlap of spirals.

It is yet another disadvantage of the known apparatus that evaporated derma is exhausted through the internal of the laser articulation arm, whereby optics and other members in the arm get dirty.

It is still another disadvantage of the known apparatus that it is very laborious to disassemble members, that may have been in contact with a patient, from the handpiece, e.g., for autoclaving.

It is still another disadvantage of the known apparatus that movement of the handpiece is restrained by the laser articulation arm, as the construction of tubes interconnected by joints is not fully flexible.

In addition, the apparatus typically has a large mass and a large inertia (typically also due to counter-balancing masses) which makes the operation and movement of the arm difficult and heavy.

Under the name Uni-laser 450P, Asah Medico A/S, Denmark, markets an apparatus for cosmetic tissue treatment, comprising a $CO_2$ laser and an optical fiber coupled to the laser at one end and to a handpiece at the other end. The laser beam is manually scanned across the treatment surface by corresponding movement of the handpiece whereby the quality of the treatment is determined and limited by the skill of the operator.

Apart from being able to accurately control the amount of light energy transmitted towards tissue to be treated, it is also desirable to be able to automatically control whether or not light is transmitted towards tissue. If, for example, a laser is pointed at healthy tissue, it is desirable that it is detected that the tissue is healthy and that transmission of a laser beam be inhibited whereby damage to healthy tissue is prevented.

It is a disadvantage of known apparatuses that the exact circumference of the surface tissue area to be treated is defined manually by the operator. Manual control easily results in accidental damage to healthy tissue due to involuntary movements of the hand.

In U.S. Pat. No. 5,531,740, an apparatus is disclosed for automatically delivering a laser beam to an intricated colored region of a treatment area, e.g. for laser photocoagulation treatment of malformed veins. Typically, venular malformation forms an extremely intricate pattern and consequently, the task of precisely delivering the laser beam exclusively to the malformed veins becomes quite formidable. During scanning over the treatment region, the color of tissue to be treated is detected and the laser automatically treats only areas having a specified color.

It is a disadvantage of the apparatus that it is bulky and cannot easily be moved into treatment positions in relation to various surfaces of a human body. Rather, a tissue surface to be treated has to be brought into a specific position in relation to the apparatus before treatment can take place.

It is still another disadvantage of the known apparatuses that the distance between the surface to be treated and the output laser beam optics is unknown so that the degree of focusing of the laser beam on the surface to be treated is dependent on the operator.

It is yet another disadvantage of known apparatuses that no feed-back on the quality of the treatment currently in progress is provided.

SUMMARY OF THE INVENTION

It is an object of the present invention to provide an apparatus for tissue treatment having a handpiece that can be moved around, i.e. traversed and rotated, freely by an operator, i.e. without exerting forces acting against the movement.

It is another object of the present invention to provide an apparatus for tissue treatment in which one or more tissue parameters at the area to be illuminated by the treating light beam is detected and in which parameters of the laser beam is adjusted according to detected tissue parameter or parameters.

It is still another object of the invention to control parameters of the treating light beam according to the detected tissue parameter or tissue parameters whereby various types of tissue can automatically be treated differently.

It is a further object of the present invention to provide an apparatus for tissue treatment that include means for detecting the distance between the surface of tissue to be treated and the output optics focusing treating light onto the surface so that optimum focusing conditions may automatically be obtained during treatment.

It is still another object of the present invention to provide an apparatus for tissue treatment that includes a temperature measuring device for measurement of tissue surface temperature.

It is yet still another object of the present invention to provide an apparatus for tissue treatment that is adapted to automatically and accurately treat tissue to a desired depth causing only a minimum of damage to surrounding tissue that are not treated.

It is a further object of the present invention to provide an apparatus for cosmetic tissue treatment that is adapted to ablate dermal cells uniformly and from a large area of a patient.

According to a first aspect of the invention, the above-mentioned and other objects are fulfilled by an apparatus for tissue treatment, comprising a light emitter for emission of a first light beam and an optical fiber for transmission of the light beam. The fiber has a beam-inlet end that is aligned with the emitted light beam so that the first light beam is coupled into the optical fiber and a beam-outlet end for emission of the transmitted light beam. Further, the apparatus comprises a handpiece coupled to the optical fiber at the beam-outlet end and comprising an output for emission of the first light beam towards a target area of tissue to be treated, deflection means for adjustable deflection of the light beam, detector means for detecting at least one tissue parameter at the target area, and first light beam control means for controlling parameters of the first light beam deflected by the deflection means in response to the detected at least one tissue parameter whereby various types of tissue can automatically be treated differently.

According to a second aspect of the invention, an apparatus for tissue treatment is provided, comprising a light emitter for emission of a first light beam and means for directing the first light beam towards a target area to be treated. The apparatus further comprises detector means for detecting at least one tissue parameter at the target area, and first light beam control means for controlling parameters of the first light beam in response to the detected at least one tissue parameter without interruption of the propagating light beam.

According to a third aspect of the invention, an apparatus for tissue treatment is provided wherein at least one tissue parameter is detected before treatment, the apparatus comprising a light emitter for emission of a first light beam and deflection means for adjustable deflection of the light beam along a predetermined path and detector means for detecting at least one tissue parameter at the target area. The apparatus further comprises storage means for storage of coherent data sets of signal values provided by the detector means at positions along the predetermined path and the respective corresponding positions thereby mapping tissue parameters as a function of stored relative positions along the path and first light beam control means for controlling parameters of the first light beam along the predetermined path in accordance with the stored data sets.

According to a fourth aspect of the invention, a handpiece for an apparatus for cosmetic tissue treatment as described above is provided, comprising an input connector for connection of a first beam-outlet end of a first optical fiber to the handpiece and for alignment of the first optical fiber with an axis of the handpiece so that a first light beam emitted from the first beam-outlet end is transmitted substantially along the axis. The handpiece further comprises an output for emission of the deflected first light beam towards a target area of tissue to be treated and detector means for detecting the type of tissue at the target area. The handpiece still further comprises first light beam control means for controlling parameters of the first light beam emitted towards the target area in response to the detected type of tissue.

According to a fifth aspect of the invention, an apparatus for cosmetic tissue treatment is provided, comprising a light emitter for emission of a first light beam, means for directing the first light beam towards a target area to be treated, detector means for detecting at least one tissue parameter at the target area, the tissue parameter being selected from the group consisting of texture, elasticity, size, and shape, and first light beam control means for controlling at least one parameter of the first light beam in response to the detected at least one tissue parameter.

Certain types of tissue, such as small marks on the tissue such as marks from chloasma, liver spots, red spots, tattoos, blood vessels, beauty spots, freckles, etc, to be treated are characterized by the shape or the size of the area covered by the type of tissue in question. For example, when treating different types of marks of substantially identical colors it may be desirable to treat each type of mark differently and according to the respective size or shape of the type of mark in question.

When the apparatus is kept in a fixed position in relation to a target surface which is illuminated by the first light beam changing of the position of the deflection means causes the first light beam to traverse or scan the target surface along a path or a curve. An area may be traversed or scanned by the first light beam, e.g. by letting the first light beam traverse or scan a meander like path substantially covering the area or, by traversing or scanning the area line by line. In the present context, the type, number and shape of paths traversed by the first light beam in order to traverse a specific area is denoted the traversing pattern or the scan pattern. The area that is scanned or traversed by the first light beam is denoted the scan area, the treatment area or the traversed area. The first light beam may treat the surface at the target area and the first light beam may therefore be denoted the treating light beam.

Cellular water absorbs light energy, and applying light energy to the cells is therefore an efficient way of ablating tissue. Thus, it is preferred to use light sources, such as lasers, generating light at wavelengths with a high absorption in water, preferably wavelengths larger than 190 nm, such as wavelengths in the range from 190 nm to 1900 nm, preferably from 700 nm to 900 nm, and even more preferred approximately 810 nm, or, preferably wavelengths larger than 1900 nm, such as wavelengths in the range from 1900 nm to 3000 nm, preferably from 1900 nm to 2200 nm, preferably from 1900 nm to 2100 nm, or, from 2800 nm to 3000 nm, and even more preferred approximately 2930 nm, or wavelengths equal to or greater than 4500 nm, such as wavelengths in the range from 4500 nm to 11000 nm, preferably from 4500 nm to 5500 nm, alternatively from 10000 nm to 11000 nm, such as around 10600 nm.

The apparatus according to the invention may be used for ablating a thin epidermal layer of the derma of a patient, removing marks on the tissue, such as marks from chloasma, liver spots, red spots, tattoos, blood vessels just below the surface, etc, as well as warts, wounds, hair follicles, etc, and hereafter the terms tissue and resurfacing will include these marks and treatments thereof.

It is preferred, that the light source utilized in the present invention is a laser, but other light sources, such as light emitting diodes and halogen bulbs, may be utilized. The laser may be any laser capable of emitting light with sufficient power for illuminated cells to vaporize, such as $CO_2$ lasers, YAG lasers, such as Erbium YAG lasers, Holmium YAG lasers, Nd YAG lasers, etc., semiconductor lasers, pulsed lasers, gas lasers, solid state lasers, Hg lasers, excimer lasers, etc.

Present $CO_2$ lasers emit light at a wavelength of 10600 nm. The $CO_2$ laser is particularly well suited as a light source in an apparatus for ablating dermal cells as water has a high energy absorbance at 10600 nm and the $CO_2$ laser is capable of reliably delivering the required laser power.

Erbium YAG lasers emit light at a wavelength of 2930 nm. Water absorbs less energy at this wavelength that at 10600 nm. Therefore, the Erbium YAG laser may be preferred for ablating thinner layers of dermal cells than may be ablated with a $CO_2$ laser. Tissue having been treated with light emitted from an Erbium YAG laser may heal faster than tissue having been treated with $CO_2$ laser light as a thinner layer of dermal cells is influenced by Erbium YAG laser light. An Erbium YAG laser may also be preferred when photocoagulation of blood vessels should be avoided.

A CO laser emits light in the 4500 nm to 5500 nm wavelength range. Water absorption at these wavelengths is somewhat less than water absorption at 10600 nm. A CO laser light source is presently preferred for dental treatment, e.g. for removal of carries, as dentine is not influenced by illumination of light from a CO laser.

A Nd YAG laser with a frequency doubled output beam in the 520–680 nm wavelength range is presently preferred as a light source for treatment of hypervasculation. Light in this wavelength range causes photocoagulation of blood without affecting surrounding tissue provided that an appropriate intensity of the light beam is directed towards the micro vessels-for an appropriate period of time. Coagulation stops blood flow in the treated vessels whereby discoloration of the skin also stops.

Typically, a power density greater than about 50 $W/mm^2$, such as a power density in the range from about 50 $W/mm^2$ to about 180 $W/mm^2$, is adequate for vaporizing cells with a minimum of damage to the surrounding tissue.

However, when removing hairs, the wavelength of the light is preferred to be approx. 800 nm. At this wavelength the absorption of the light in the hair follicles is lower than at higher wavelengths, and the power density must therefore be higher than 180 $W/mm^2$, preferable higher than 300 $W/mm^2$. Generally, the power density is adapted to the wavelength and the tissue to be treated.

The optical fiber for interconnection of a light source with a handpiece according to an embodiment of the present invention may be any fiber, such as a poly-crystalline silver halide fiber, etc, that is suitable for transmission of light emitted from the light source and that is made of a material that allows repeated bending of the fiber, so that an operator can freely manipulate the handpiece in order to direct the light beam towards various areas of a patient.

A handpiece is a single unit for conveniently holding in one hand by an operator of the handpiece.

It is preferred to shape the handpiece ergonomically so that a comfortable hand grip is provided for the operator of the apparatus. For example, it is preferred to direct the light beam towards a target area at a substantially right angle to the area. The ergonomic form of the handpiece allows the operator to point the light beam at a substantially right angle to the target surface without having to bend the wrist in an uncomfortable way.

Preferably, the handpiece is light so that it is easy for the operator to hold the handpiece and bring it into any desired position in relation target surface to be treated. The weight of a preferred handpiece according to the present invention—cables and fibers not included—is less than 500 grams, such as 290 grams, or such as 250 grams.

User interface means may be provided for selection of parameters relating to the operation of the apparatus. According to a preferred embodiment of the invention comprising a handpiece, the user interface means are positioned on the housing of the The parameters may comprise traversing velocity of the output light beam from the handpiece, intensity of the output light beam emitted form the handpiece, size of the target surface area to be traversed by the output light beam, shape of the target surface area to be traversed by the output light beam, etc.

The user interface means may comprise a first button, e.g. a membrane switch, for selection of a parameter type by stepping through a set of parameter types, such as the set listed above or any subset thereof.

The user interface means may further comprise a second button, e.g. a membrane switch, for selection of a parameter value of the parameter type currently selected by stepping through a corresponding set of parameter values.

A set of light emitting diodes may be provided for indication of the set of currently selected parameter values.

It is an important advantage of provision of the user interface at the handpiece that an operator of the handpiece is able to simultaneously select operational parameters of the handpiece and observe resulting changes in treatment effects as the operator is not forced to shift his field of view from the surface area to be treated to a user interface panel positioned somewhere else, e.g. behind the operator.

Preferably, the buttons are positioned on the housing of the handpiece so that single-handed operation is possible, preferably, with the right as well as with the left hand.

The user interface means may further comprise a foot pedal. The first light beam traverses a target surface area when the operator depresses the pedal. Preferably, first light beam traversing is stopped immediately when the operator releases the pedal and the emission of the first light beam towards the target surface area is prevented.

As already mentioned, it is desirable to automatically control whether or not tissue towards which the first light beam is directed or towards which the handpiece is directed (the handpiece is said to be directed towards a specific area if that area is illuminated when the light beam emitted by the handpiece is turned on) is treated and to what extend it may be treated. For example, if the first light beam or the handpiece is directed towards healthy tissue, turn on of the first light beam may be inhibited or the laser parameters may be controlled so that no damage will be induced in the healthy tissue.

Tissue may be classified into specific tissue types according to predetermined values of various parameters, such as color, temperature, texture, elasticity, size, shape, etc.

For example, various marks may be detected by their color. Thus, the detector means may comprise light detectors for detection of intensity of light emitted from tissue at the target area, the target area being the area to be treated by the first light beam or being the area the handpiece is currently directed at.

The light detector is preferably a semiconductor light detector, such as a photodiode, etc.

The light detector means may be positioned inside the handpiece.

The target area may be illuminated by a light source, such as a white light source, and the reflected light from the target area may be detected by the detector means and analysed so as to characterise the type of tissue that is illuminated.

Further, light sources emitting light of different predetermined wavelengths may be directed towards the target area. For example, the light sources may comprise two light emitting diodes, one for emission of light in the wavelength range where the light is considered red and the other for emission of light in the wavelength range where the light is considered green. Also the light sources may comprise three, four or even more light emitting diodes for emission of light of different wavelength ranges. The light sources may alternatively emit light in the ultra violet or infrared wavelength range. Light from the light sources is transmitted towards the target area and is reflected by tissue at the target area. The reflected light is detected by the detector means and the intensity of reflected light in the two or more wavelength ranges in question characterizes one or more parameters of tissue that is illuminated.

The light source or light sources illuminating the target area may be positioned inside the handpiece.

The first light beam control means comprises outputs for controlling various parameters of the first light beam emitted by the light emitter, such as wavelength, output power, duty cycle, etc. Based on tissue parameter or tissue parameters as measured by the detector means, the first light beam control means adjusts parameters of the emitted light correspondingly. For example, when two light sources are utilized for detection of tissue parameters as previously described, predetermined reflected light intensity value ranges for the two wavelength ranges may be stored in a memory of the first light beam control means. During treatment, measured values of reflected light intensity are compared with the stored predetermined ranges and when measured values are within the stored ranges treatment is enabled and otherwise it is disabled.

Treatment may be disabled by stopping the emission of the first light beam by shutting off the light emitter or by inserting a shutter in the path of the first light beam. Alternatively, the parameters of the light emitter emitting the first light beam may be controlled so that tissue at the target area is not influenced by the first light beam.

Further, the wavelength and/or the power of the first light beam emitted by the light emitter may be adjusted according to the measured values. For example, a plurality of predetermined ranges of reflected light intensity may be stored in the memory and during treatment the measured values may be compared to the stored ranges and the value of the wavelength and/or the power of the first light beam may be set according to relations between measured values and stored ranges. Alternatively, the first light beam control means may calculate and control the wavelength and/or the power of the first light beam as a predetermined function of measured values of reflected light.

The output power of the first light beam may be adjusted by adjustment of the continuous output power of the light emitter, by adjustment of the duty cycle of the light emitter, etc.

The apparatus for tissue treatment may comprise an infrared detector, such as an infrared photo detector, for detection of intensity of infrared light emitted from tissue at the target surface, e.g. for determination of the temperature of the tissue. Like color, temperature may be utilized for characterization of tissue types. Further, tissue temperature may be utilized for monitoring of treatment progress and quality. The temperature of treated tissue increases during treatment and measurement of tissue temperature may be utilized for verification of the effect of the treatment. For example, when a specific tissue temperature is reached within a specific area, treatment of that tissue may be terminated, e.g. further treatment may be inhibited, as sufficient treatment has already been accomplished. Further, if a certain temperature has not been reached during treatment, output power of the light emitter may be increased to increase efficiency of the treatment.

The infrared detector may be positioned in the handpiece.

Furthermore, a cooling fluid, such as water, such as a gel, etc. may be applied to the surface to be treated during treatment. For example, the fluid may be applied between two plates of a material transparent to the light beams to be used during treatment. The fluid may be positioned in a substantially closed reservoir between the two plates or the reservoir maybe provided with an in-let and an out-let whereby the fluid may pass through the reservoir to ensure constant cooling during treatment.

Thus, the apparatus may comprise a cooling member that is adapted to be positioned at the target area for cooling of tissue at the target area and that is at least partly transparent to the first light beam. The cooling member may comprise a frame, an upper window positioned in the frame, and a lower window positioned in the frame, the frame, the upper window, and the lower window defining a volume therebetween for receiving and holding a cooling liquid. Further, the cooling member may comprise an inlet for inputting cooling liquid to the volume and an outlet for outputting cooling liquid from the volume. The cooling member may be attached to the handpiece.

To obtain an optimum result of treatment, it is important to keep the light beam focused at the target area during treatment.

The apparatus may comprise means for automatically controlling the distance from the apparatus to the focus point in such a way that the light beam is automatically focused at the target area during treatment. For example, if the handpiece comprises the means for automatically controlling, the distance from the handpiece to the focus point is controlled.

Thus, the detector means may comprise a detector array and array optics for forming an image of the target area on the array. Further, the detector means may comprise image processing means for processing output signals from the defector array.

Preferably, the image processing means is adapted to calculate the size of a spot on the target area illuminated by the first light beam, or another light source of the apparatus, and imaged onto the detector array.

The apparatus may further comprise output optics for focusing the first light beam onto the surface of tissue to be treated and movably positioned at the output of the apparatus for adjustment of the distance between the apparatus and the focus point, and focus control means for adjusting the position of the output optics in response to the value of the calculated spot size.

For example, the handpiece may comprise the output optics for focusing the first light beam onto the surface of tissue to be treated whereby the distance between the handpiece and the focus point is adjusted by adjusting the position of the output optics in response to the value of the calculated spot size.

According to another embodiment of the invention, two crossing visible light beams are emitted from the handpiece, the cross point of the beams indicating the focus point of the first beam. The image processing means are adapted to detect the number of spots imaged onto the detector array, and the focus control means are adapted to adjust the position of the output optics in response to the number of spots and, preferably, the distance between them (if more than one).

The deflection means may comprise any optical component or components suitable for deflecting light of the wavelength in question, such as mirrors, prisms, diffractive optical elements, such as holograms, grids, gratings, etc, etc.

The means for directing may comprise any optical component or components suitable for directing light of the wavelength in question, such as reflective elements, such as mirrors, etc, refractive elements, such as prisms, lenses, etc, diffractive optical elements, such as holograms, grids, gratings, etc, etc.

Further, the handpiece may comprise the deflection means.

The deflection means are preferably adjustably mounted for displacement of the deflection means as a function of time, so that the first light beam may traverse a surface along a predetermined path, while the apparatus is kept in a fixed position. Preferably, the deflection means are rotatably mounted, and the actual deflection of the light beam is determined by the current angular position of the deflection means. This is a particular advantage when the handpiece comprises the deflection means as the handpiece then may be kept in a fixed position during traversing of the surface target area whereby traversing of the surface is not depending on operator skills. Moving means may be utilized to control positions of the deflection and focusing means, such as actuators, such as piezo electric crystals, the displacement of which is controlled by applying a specific electric voltage to their electrodes, electromotors generating linear or rotational displacements, galvanometers, magnetically activated or controlled actuators, pneumatic actuators, hydraulic actuators, etc.

The positions of the deflection means may be controlled by deflection control means adapted to control the deflection means to deflect the light beam in such a way that it traverses a target surface along a predetermined path.

According to an embodiment of the invention, an apparatus is provided, having two mirrors that are rotatably mounted in the path of the light beam in the apparatus. The rotational axis of the mirrors may be substantially perpendicular to each other in order to obtain two dimensional deflection of the light beam. Further, a handpiece may be provided having the two mirrors rotatably mounted in the path of the light beam in the handpiece.

Alternatively, the deflection means may comprise one mirror that is rotatable around two axes that may be substantially perpendicular to each other.

The mirrors may be connected to electromotors for angular positioning of the mirrors, e.g. each mirror may be directly connected to a corresponding shaft of a motor, whereby each motor is used for angular positioning of the corresponding mirror.

In order to minimize the size of the handpiece, it is preferred to mount the motors with their respective shafts in a common plane. For example, one motor may be a linear motor, such as a linear step motor, generating linear displacements. The shaft of this motor may be connected to the mirror at a first edge of the mirror, while a second and opposite edge of the mirror is rotatably connected to the handpiece. By pushing or pulling the first edge by the linear motor, the mirror is rotated about its rotational axis. The other motor, preferably a galvanometer, may be connected to the other mirror in the conventional way described above, whereby the two mirrors may be rotated around substantially perpendicular axes.

The deflection control means may be adapted to control the deflection means so that the predetermined path is a substantially straight line.

Preferably, the deflection control means are adapted to control the deflection means so that the light beam traverses a target surface area line by line.

It is an important advantage of the line by line traversing pattern that areas of any arbitrary shape, such as polygonal, such as rectangular, quadratic, triangular, etc, or circular, elliptic, etc, may be traversed line by line by appropriately controlling the starting point and stopping point of light emission along each line traversed.

Preferably, the first deflection control means are adapted to control the first deflection means so that the lines are traversed sequentially i.e. neighbouring lines are traversed successively. This minimizes the requirement for the operator to be able to keep the handpiece steady in a desired position because when lines are traversed successively, neighbouring lines are traversed within a very short time period so that involuntary hand movements of the operator does not lead to traversing overlap i.e. involuntary hand movements can not within the very short time period during which a single line is traversed move the handpiece back to the line previously traversed which would lead to uneven treatment of the target surface.

If an interlacing traversing pattern were utilized, i.e. every second line of the target surface area is traversed and after that the remaining lines in-between are traversed, there would be sufficient time between traversing of neighbouring lines to allow involuntary movements of the handpiece to a line previously traversed leading to repeated treatment of one area that may damage tissue at that area and leaving another area without treatment.

Thus, a method is provided of traversing a light beam across an area of a tissue, comprising the steps of emitting the light beam towards the tissue area, deflecting the light beam with deflection means so that the tissue is traversed by the light beam line by line sequentially, each line being traversed in the same direction.

The first deflection control means may be adapted to control the first deflection means so that the lines are traversed in the same direction whereby substantially the same amount of power per area is delivered uniformly across the target surface area leading to substantially the same temperature increase at any point of the target surface area after traversing.

When a target area is traversed line by line, it is preferred that movement of one mirror causes the light beam to traverse a line while movement of the other mirror moves the light beam to the next line. In the example above, the galvanometer preferably generates the line traversing as the galvanometer can move the mirror at a high speed, and the linear motor preferably generates the displacement of the light beam to the next line to be traversed.

As mentioned earlier, it is preferred to control the amount of energy delivered to cells to be ablated, as the amount of energy must be sufficient for the dermal cells to vaporize and, simultaneously, the amount of residual energy heating non-ablated cells must be so low that non-ablated cells will not be seriously damaged. Thus, when an area of tissue is traversed, e.g. line by line, it is preferred that neighbouring lines substantially abut each other. Clinical investigations have shown that, typically, an overlap of 0.1 to 0.2 mm is acceptable, and a distance between traversed lines of up to 0.1–0.2 mm is acceptable.

In order to control positioning of paths on the target area this accurately, it is preferred to position the deflection means extremely accurately e.g. in the handpiece. In the preferred embodiment of the invention, this is accomplished by utilisation of printed circuit technology providing high accuracy of hole positioning of 0.05 mm. The mirrors are rotated around shafts that are mounted in printed circuit boards providing the required positioning accuracy. Further, the motors rotating the mirrors are also mounted on the printed circuit boards providing electrical connections to the motors and the mechanical support and positioning needed.

When traversing a target surface area line by line, it is preferred to traverse each line in the same direction ensuring uniform heating of cells across the target surface area. Further, it is preferred to turn off the light beam, e.g. by switching off the light emitter, by inserting a light obstructing member in the light path of the beam, etc, while the light beam is moved from the end of a line having been traversed to the start of the next line to be traversed, in order to avoid repeated illumination of areas of the two lines.

Instead of turning the light emitter off, the light beam may be moved at a speed significantly larger than the traversing speed, during movement from the end of a line to the start of the next line.

Typically, the intensity within the beam of a light beam as generated by the light emitter varies as a normal function of the distance from the centre of the beam. The optical fiber may be designed or selected to be dispersive in such a way that the intensity function of the light beam emitted from the fiber as a function of the distance to the centre of the beam is substantially rectangular, i.e. the intensity of the beam leaving the fiber decays more slowly towards the edge of the beam than the intensity of a beam as generated by the light emitter whereby heat is more uniformly generated in cells across a traversed fine of tissue.

The detector means may be utilized for detection of various tissue parameters during scanning of the first light beam across a tissue area so that treatment and tissue parameter determination are performed substantially simultaneously including adjustment of light beam parameters according to detected tissue parameter values.

However, it is presently preferred that the light beam control means further comprises switching means for preventing emission of the first light beam and being controlled by the first light beam control means so that emission of the first light beam is prevented during a detecting scan from a predetermined first position to a predetermined second position along a predetermined path. During the detection scan the detector means detect light reflected from the target surface area along the predetermined path and the reflected light is analysed by the detector means or alternatively the reflected light is analysed by a microprocessor common to the controlling means analysing means of the apparatus.

The apparatus may further comprise tissue parameter storage means, such as an EEPROM, for storage of coherent data sets of signal values provided by the detector means at predetermined positions along the predetermined path of the light beam and the corresponding positions of the deflection means thereby mapping tissue parameters as a function of relative position within the target area of the tissue in the storage.

The storage means may comprise any memory, such as an electronic memory, such as an EEPROM.

The first light beam control means may further be adapted to control parameters of the first light beam during a second movement of the light beam along the above-mentioned predetermined path in accordance with the coherent data sets stored.

For example, without automatic control of tissue treatment, removal of hair is a difficult task to perform as a large number of small spots having diameters of approximately 1 mm have to be pinpointed by the operator performing the treatment. According to the present invention, the surface tissue area with hair to be removed is scanned by the apparatus, e.g. the handpiece. Hereby the hair follicles are detected by color determinations as described above and their positions along the scanned path of the light beam are stored in the tissue parameter storage means. During a second and repeated scan of the tissue area, the first light beam is turned on and off according to the content of the tissue parameter storage means so that solely the hair follicles detected during the first scan are treated preventing the surrounding tissue from being damaged. Alternatively, the parameters of the first light beam are regulated according to the content of the tissue parameter storage means so that in a first position the power-per-area of the light beam is adjusted so that the detected hair follicles are treated and in a second position the power-per-area of the light beam is reduced so that the surrounding healthy tissue is not damaged.

Parameter values, such as color, temperature, etc, stored in the tissue parameter storage may be displayed on a display unit, such as a CRT, LCD, etc, e.g. as graphical three dimensional plots showing surface profiles of the actual parameters of scanned areas. Further, the parameter values may be processed, e.g. providing averages, weighted averages, correlation, cross-correlation, etc, and the value may be displayed, e.g. on the display unit or, on a separate display on the handpiece.

By pulse width modulating the light emitter; energy delivered to the target surface may be varied along a traversed line in addition to the variations created by adjustment of parameters of the first light beam in response to detected tissue parameters. A fade-in area may be created by starting traversing of each traversed line with short pulses of light between longer periods of no light. As the line is traversed, the duration of the light pulses may be increased while the periods with no light may be decreased. Outside the fade-in area, the light beam may not be pulsed whereby the remaining part of each line is traversed with a constant intensity of the light beam.

Likewise, a fade-out area may be created by after having traversed a part of a line with constant light intensity, pulse width modulating the light source to transmit shorter and shorter pulses of light towards the line at the target surface area ending with no light transmitted at the end of the line.

The maximum amount of energy delivered by the first light beam to the target area is determined by the fade-in or fade-out function and can not be exceeded by the adjustment of parameters of the first light beam. However, the adjustment may result in a amount of energy delivered that is lower than the maximum amount of enegy.

The fade-in or fade-out traversing patterns may also be created by gradually increasing or decreasing, respectively, the power of the light source, or by decreasing or increasing, respectively, the traversing speed of the light beam.

Alternatively, a combination of these methods may be used.

The shape of the traversed area including the fading area may for example be polygonal, such as rectangular, quadratic, triangular, etc, circular, elliptic, etc.

A traversed line with fade-in and/or fade-out provides a smooth transition from a non-ablated area of tissue to an ablated area of tissue. This is a particularly advantageous feature when the apparatus according to the present invention is used for treatment of small marks on the tissue such as marks from chloasma, liver spots, red spots, tattoos, blood vessels etc.

Light intensity control means may be provided for generating a control signal for transmission to a light emitter interconnected with the optical fiber and controlling intensity of light emitted by the light emitter and transmitted through the optical fiber.

The fade-in and fade-out may be provided by controlling the intensity of the light beam and/or the velocity of the traversing light beam along a predetermined path and the light intensity control means andlor the deflection control means may be adapted to provide fade-in and fade-out.

The light intensity control means and/or the deflection control means may be adapted to control the intensity of the light beam and/or the velocity of the traversing light beam along a predetermined path as a function of the position of the light beam inside the area of the target surface area.

To provide the normal ablating of tissue, the light intensity control means may be adapted to provide a substantially constant intensity of the light beam and the deflection control means may be adapted to provide a substantially constant velocity of the traversing light beam when the traversing light beam is inside a first part of the target surface area.

If desired, the fade-in and fade-out effect may be provided either by scanning the light beam with a velocity larger than the substantially constant scan velocity within the treatment area of tissue or, by decreasing the output power of the first light beam.

The first light beam control means may be adapted to control the power-per-area of the light beam when scanned along a predetermined path on a target tissue area to be treated. For example, when ablating tissue it is presently preferred to maintain the power-per-area of the first light beam inside a first part of the target tissue area at a substantially constant level.

In order to create the fade-in or fade-out effect, the power-per-area of the light beam when outside a first part of the target tissue area may depend on the distance to the first part of the target tissue area, and it is preferred that the power-per-area of the light beam increases with decreasing distance to the first part of the target tissue area.

Keeping the intensity of the light beam substantially at the constant level as provided inside the first part of the target tissue, fade-in and fade-out may be provided by traversing the light beam with a velocity larger than the substantially constant traversing velocity within the first part of the target tissue area.

Likewise, keeping the velocity of the traversing light beam substantially constant inside the first part of the target tissue, the fade-in and fade-out may be provided by emitting a light beam with a smaller intensity than the substantially constant intensity of light emitted within the first part of the target tissue area.

The light intensity control means and/or the deflection control means may be adapted to provide a varying Intensity of the light beam outside the first part of the target surface area. The intensity of the light beam may be varied between a first intensity being substantially identical to the substantially constant intensity in the first part of the target tissue area and a second intensity being an intensity at substantially zero, i.e. no light is emitted from the output of the handpiece or the second intensity may be an intensity of which no damage is injured in the tissue.

The user interface means may also enable selection of parameters relating to fade-in and fade-out, such as traversing velocity of the output light beam from the apparatus, e.g. the handpiece, in the fade-in or the fade-out area, intensity of the output light beam emitted from the apparatus in the fade-in or the fade-out area; size of fade-in or fade-out areas, shape of fade-in or fade-out areas, etc.

In the case where the first light beam is invisible, e.g. utilizing an infra red emitter, an ultra violet emitter, etc, a light source generating visible light may be provided for generating a visible light beam that is used to assist the operator by indicating areas towards which the invisible and treating light is directed during traversing. For example, the input connector of the handpiece may be further adapted to connect a second beam-outlet end of a second optical fiber for transmission of a visible light beam to the handpiece. The second optical fiber is preferably properly aligned in the connector in relation to the predetermined path of the visible light. The handpiece may further comprise second deflection means for adjustable deflection of the visible light beam in such a way that the first light beam and the visible light beams emitted from the output of the handpiece illuminate substantially the same area of a target surface.

Further, two crossing visible light beams may be emitted from the apparatus or the handpiece, the cross point of the beams indicating the focus point of the first light beam.

Preferably, common deflection means are utilised for deflection of all light beams emitted from the apparatus or the handpiece whereby tracking of the light beams are easily accomplished. The deflection means may thus comprise Zinc selenite lenses, as they are transparent for visible light as well as for infra-red light.

In order to further assist the operator of the apparatus, the visible light beam may, e.g. between traversing with the first light beam, be traversed around at least a part of the circumference of the target surface area thereby indicating the size, shape and position of the target surface area to be traversed with the first light beam.

When a polygonal shape of the target surface area has been selected, the visible light beam may, e.g. between traversings by the first beam, be scanned along one edge of the polygon.

Thus, the method may further comprise the step of transmitting a visible light beam towards the target surface area utilizing the first deflection means.

The method may further comprise the step of traversing the visible light beam along at least a part of the circumference of the target surface area to be traversed by the first light beam.

In order to further assist the operator of the apparatus, the temperature of the target tissue area may be measured immediately after treatment. The surface temperature is measured by measuring the infrared irradiation from the surface with an infrared detector, which may be comprised in the detector means of the handpiece. This temperature provide an objective measure of the quality of the treatment. A high temperature in the surface skin indicates that the energy has been absorbed in the surface tissue, whereas a low surface temperature indicates that the energy has been absorbed in the depths of the tissue. It is also possible to provide an interface to a PC (or any other calculating unit) for further calculations on the temperature data.

In order to still further assist the operator of the apparatus in keeping a constant distance from the output of the handpiece to the surface of the tissue to be ablated, the handpiece may comprise a distance member connected to the handpiece at the output with fastening means.

As the distance member will touch the patient, it is desirable to insert a new, disinfected member before treatment of a new patient and thus, it is preferred that the fastening means comprises a magnet so that a used distance member can easily be disconnected from the handpiece, e.g. for autoclaving, and so that a new member can easily be connected to the handpiece.

In order to increase the ease of use of the apparatus, which may be on the form of a handpiece, it may be provided with interfacing means for selection of parameters of the cosmetic treatment apparatus. The interfacing means may comprise push buttons, selectors, rotary switches, etc. The interfacing means may also comprise a display for showing the mean temperature of the surface immediately after the treatment.

The parameters selectable from the apparatus may comprise the scan velocity, the ablating and the visible light beam intensities, the size and shape of the scan area, and fade-in and fade-out effects.

The apparatus according to the present invention may further comprise a processor for control of the apparatus and comprising one or more control means, such as deflection control means, light beam control means, light intensity control means, etc. The processor may further be connected to the user interface means and may be adapted to control the functions of the handpiece in accordance with the user interface selections.

Thus, the processor may be adapted to control energy density received by the target surface when traversed by the invisible treatment light beam.

Further, the processor may be adapted to control energy density received by the target surface at a specific position as a function of the position along a predetermined path traversed by the first light beam e.g. in order to provide fade-in and fade-out.

According to a preferred embodiment of the invention the processor means may be positioned inside the handpiece.

The processor may comprise a memory, such as an EEPROM, for storing of different parameters of traversing patterns and fade-in and fade-out patterns, such as target surface area size, traversing duration, etc. Further the processor means may comprise the storage means for storage of coherent data sets of signal values provided by the detector means at positions along the predetermined path and the respective corresponding positions thereby mapping tissue parameters as a function of stored relative positions along the path.

The apparatus, e.g. in the form of a handpiece may further be provided with a computer interface facilitating reception of traversing pattern parameters generated in a computer and transmitted to the apparatus for storage in the memory. The user interface may be utilized for selection of a specific traversing pattern from the set of patterns stored in the memory as previously described. The computer may be any programmable electronic device capable of storing, retrieving and processing data, such as a PC.

It is an important advantage of provision of a processor in the handpiece that signal lines between the handpiece and an external device controlling the handpiece are not needed. This reduces weight of the handpiece with cables connected. Further, electrical noise on control lines is minimized because of reduced lengths of the lines. Still further, control speed is increased as capacitance of a short line is small.

Various traversing patterns may be created on a PC and be downloaded to the memory of the handpiece. The patterns may be stored in the form of a table of parameters defining number of lines, length of lines, distance between lines, start and end points of fade-in and fade-out of each line, points of turn on and turn off of the traversing light beam, etc of each traversing pattern stored.

A traversing pattern box may be provided, containing a processor, a memory and interface means for storage of traversing patterns generated, e.g. on a PC and transmitted to the box through the interface means for storage in the memory. The interface means of the box and the computer interface of a handpiece may be interconnected and the various traversing patterns stored in the box may be transferred to the memory of the handpiece whereby traversing patterns created at a single PC may be distributed to a plurality of handpieces that may be situated remotely from the PC.

BRIEF DESCRIPTION OF THE DRAWINGS

In the following, a preferred embodiment of a cosmetic tissue treatment apparatus comprising detector means will be described with reference to the drawings, wherein.

DETAILED DESCRIPTION OF THE DRAWINGS.

Figure 1:
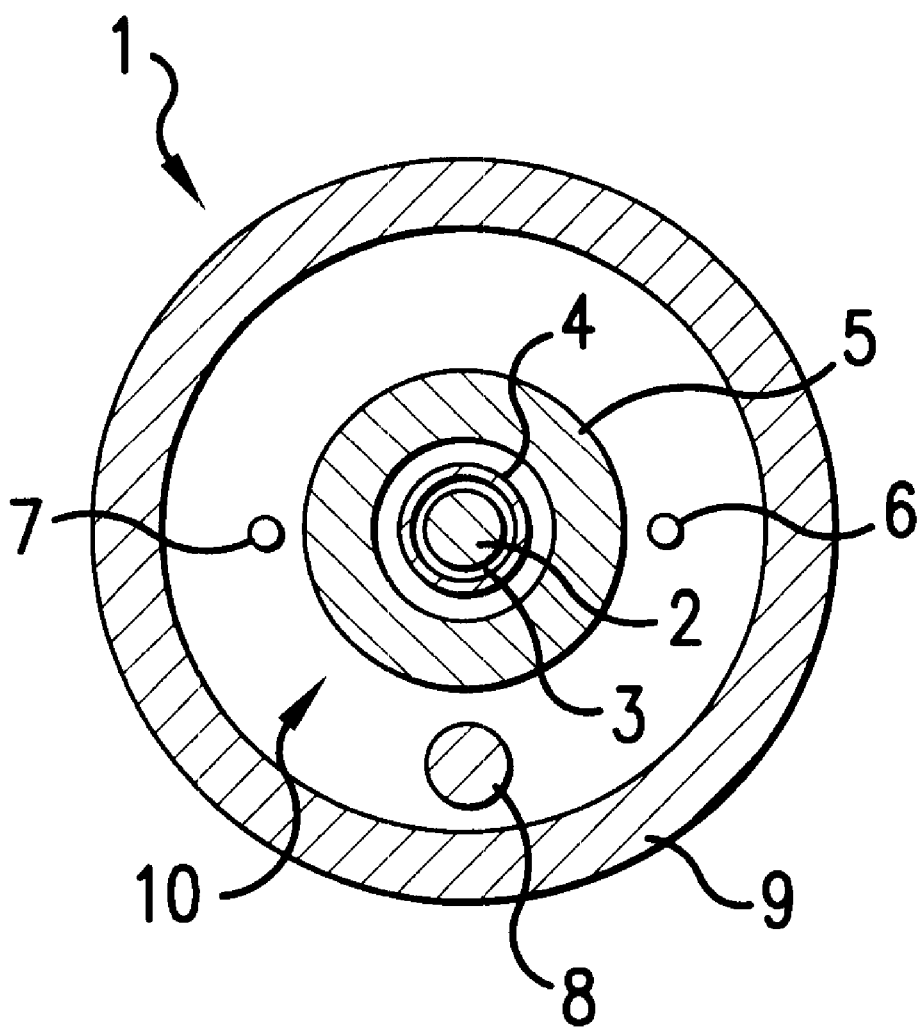
FIG. 1 shows a cross section of a cable for transmission of light from a laser source to the handpiece.

FIG. 1 shows a cross section of a cable 1 for transmission of light from a laser source to the handpiece of an apparatus for cosmetic tissue treatment according to the present invention. An optical fiber 2 is positioned at the centre of the cable 1. The optical fiber 2 is made of silver chloride and silver bromide (silver halide), which is especially designed for transmission of light at a wavelength of app. 10.6 $\mu$m. The optical fiber 2 is covered by a cladding 3 which is also made of silver bromide and silver chloride but mixed in another ratio. The cladding prevents light travelling in the fiber 2 from escaping from the fiber 2. The diameter of the fiber 2 is app. 500 $\mu$m, and the cladding 3 is app. 50 $\mu$m thick. The fiber 2 and the cladding 3 are protected against the environment by a teflon tube 4. The fiber 2 and the cladding 3 are also protected against mechanical stress by a plastic tube 5 also protecting the teflon tube 4. The fiber 2, the cladding 3, the teflon tube 4 and the plastic tube 5 constitutes an optical fiber unit 10. The cable 1 further comprises two glass fibers 6, 7 and a wire 8. The two glass fibers 6, 7 have a small NA (numerical aperture) designed for propagation of visible light at a wavelength of app. 650 nm. The wire 8 is provided for protecting the cable 1 against tensions and overloads. The optical fiber unit 10, the two glass fibers 6, 7, and the wire 8 are enclosed by a spiral tube 9 made of stainless steel. The optical fiber unit 10, the two glass fibers 6, 7, and the wire 8 are not fixed in position relative to each other inside the spiral tube 9, but can move in relation to each other, e.g. during bending of the cable 1. This makes the cable 1 very flexible when it is moved, and it provides at the same time a good protection of the fragile fibers 2, 6, 7. Compressed air is blown along the optical fiber unit 10 inside the spiral tube 9. The compressed air exits the handpiece in front of the optics, thereby preventing any ablated material from depositing on the optics.

A first light beam emitted by a $CO_2$ laser is coupled into the optical fiber 2 at beam inlet end of the fiber 2 positioned at one end of the cable 1. At the beam-inlet end of the cable 1, second light beams from two diode lasers are coupled into the glass fibers 6, 7, respectively. The first and second light beams propagate through the respective fibers 2, 6, 7 from the respective beam-inlet end to the respective beam-outlet end, which is connected to a handpiece 38.

Figure 2:
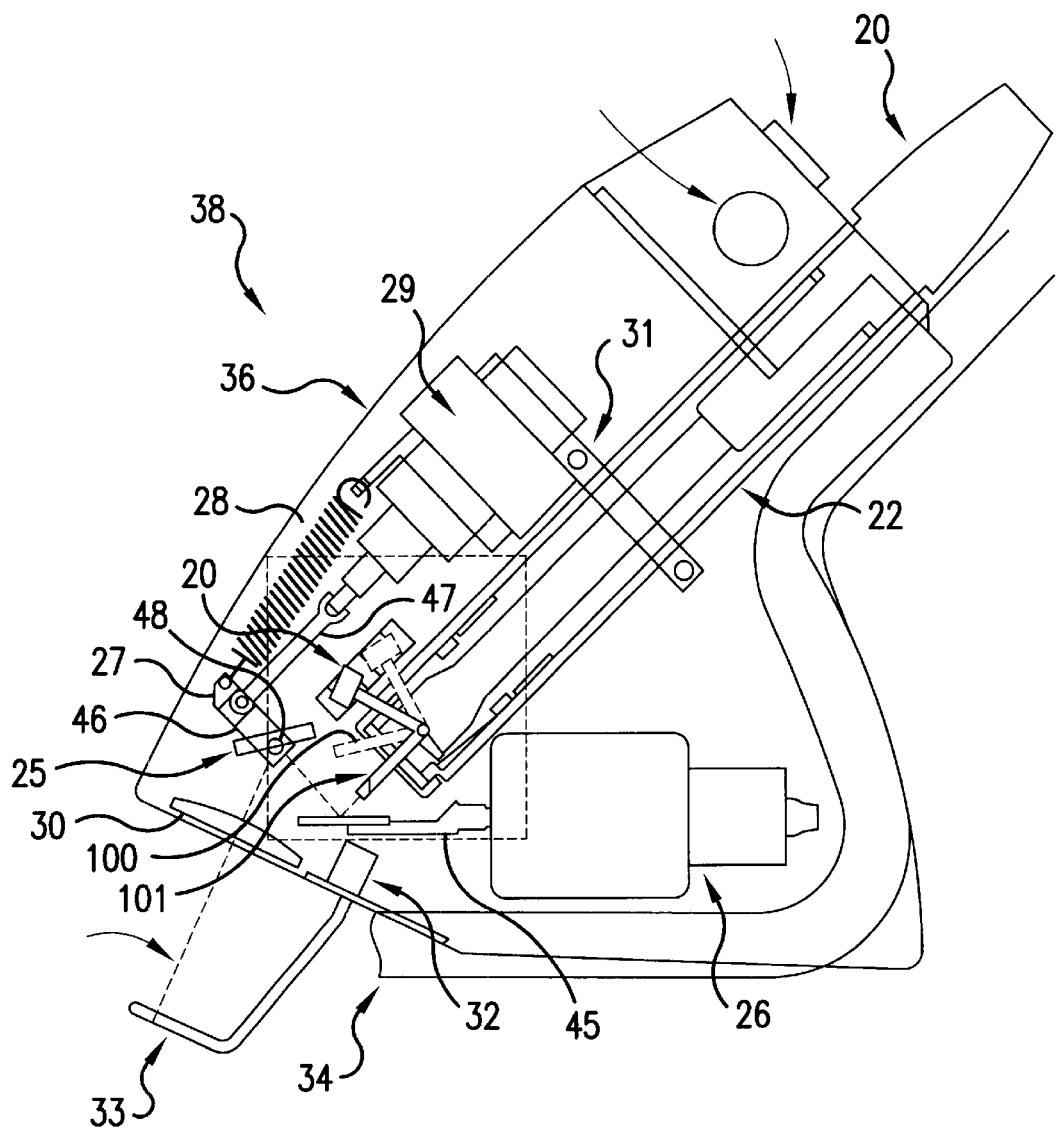
FIG. 2 shows a cross section of a handpiece according to the present invention.

FIG. 2 shows a handpiece 38 of an apparatus for tissue treatment according to the present invention. The cable 1 (not shown in FIG. 2) is connected to the handpiece 38 at a fiber inlet member 20, and is guided through a tube 22 which is held in place in the handpiece 38 by the holding and heat distributing means 31. The fiber inlet member 20 also serves as a cable protecting sleeve. The light beams transmitted in the optical fiber 2 and the two glass fibers 6, 7 respectively are radiated from the respective beam-outlet ends of the fibers 2, 6, 7 through a lens system 39—shown in greater detail in FIG. 3—towards an object, e.g. a human tissue surface. Each of the beam-outlet ends of the fibers 2, 6, 7 is positioned at a distance appropriate for the focusing lens 21 to focus the light from the fiber in question 2, 6, 7 on the object.

Figure 3:
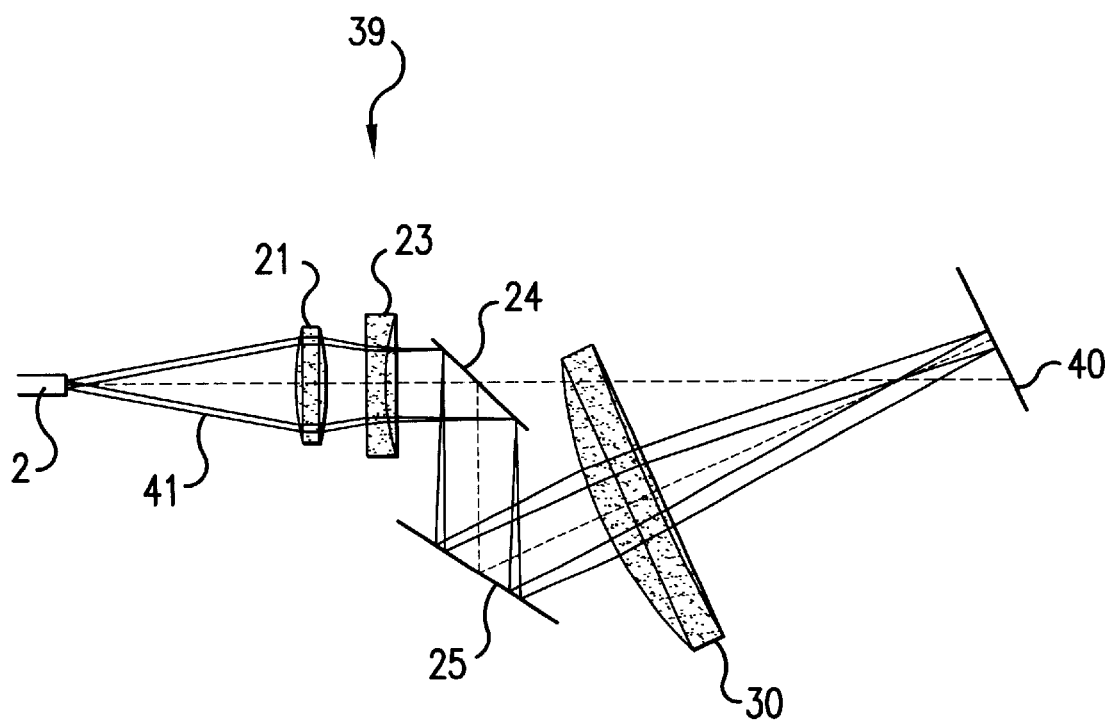
FIG. 3 shows the lens system of the handpiece shown in FIG. 2 in treatment mode in greater detail.

In FIG. 3, the lens system 39 is shown in greater detail. The first and second light beams radiated from the beam-outlet ends of the fibers 2, 6, 7 are focused by the first focusing lens 21 and collimated by the collimating lens 23. The collimated light beams are transmitted from the collimating lens 23 via deflection means comprising a first mirror 24 and a second mirror 25 to a second focusing lens 30 which focuses the light beams on the target 40, which e.g. can be the facial tissue of a human being. The distance between the focusing lens 30 and the focus plane at the object 40 is preferably approx. 27 mm.

The first deflection means also constitute the second deflection means and comprise the first mirror 24 that is mounted on the first deflection means that also constitute the second deflection means and comprise a galvanometer 26 with an indicator 45 and positioned in the handpiece 38 of the handpiece according to the invention. When an electric current is driven through the coil of the galvanometer 26, the magnetic field generated by the current will make the indicator 45 rotate around the longitudinal axis of the indicator 45. The first mirror 24 will thereby be rotated, and the light beams will be deflected at an angle twice the angle rotated by the mirror 24 in relation to the first light beam. The positioning resolution of the galvanometer 26 is limited by the electronic deflection control means controlling the galvanometer 26 to 255 positions.

The first deflection means also comprise the second mirror 25 mounted on an arm 46 actuated by a linear actuator 29 comprised by the first deflection means. When the linear actuator 29 activates the actuator arm 47, the arm 46, and thereby the second mirror 25, is rotated around the shaft 48. A spring 28 is connected to one end of the arm 46 and to a non-moving part of the linear actuator 29 in the other end so as to prevent wobble around the shaft 48. When the second mirror 25 is rotated around the shaft 48, the light incident on the second mirror 25 is deflected an angle that is twice the angle rotated by the mirror 25. The linear actuator 29 may be controlled by applying a sequence of pulses across the terminals (not shown) of the actuator 29. The positioning resolution of the linear actuator is discrete and limited to a maximum number of steps of approx. 200.

The optics of the apparatus limits the possible,scan area to approx. 10*10 mm, corresponding to an angular displacement of the mirror 24 of approx.±8° and an angular displacement of the mirror 25 of approx.±5°, even though the maximum movement of the mirror 24 is approx.±11° and the maximum movement of the mirror 25 is approx.±10°. The extra possible movement which is not used during scanning is used during start-up of the system to ensure accurate and reliable speed before the treatment scan is started.

By controlling the current to the coil of the galvanometer 26 and the pulse sequence applied across the terminals of the linear actuator 29, the direction of light beams emitted from the focusing lens 30 towards the target 40 can be controlled. It is thus possible to create different kinds of scan patterns of the light beam, such as rectangular or circular scan patterns.

An arm 100 with a mirror 101 is rotatably mounted for rotation by a solenoid 109. In one position the mirror 101 is positioned in the beam path of the first laser light beam when the optical system is in a sensing mode as explained further below.

Figure 4:
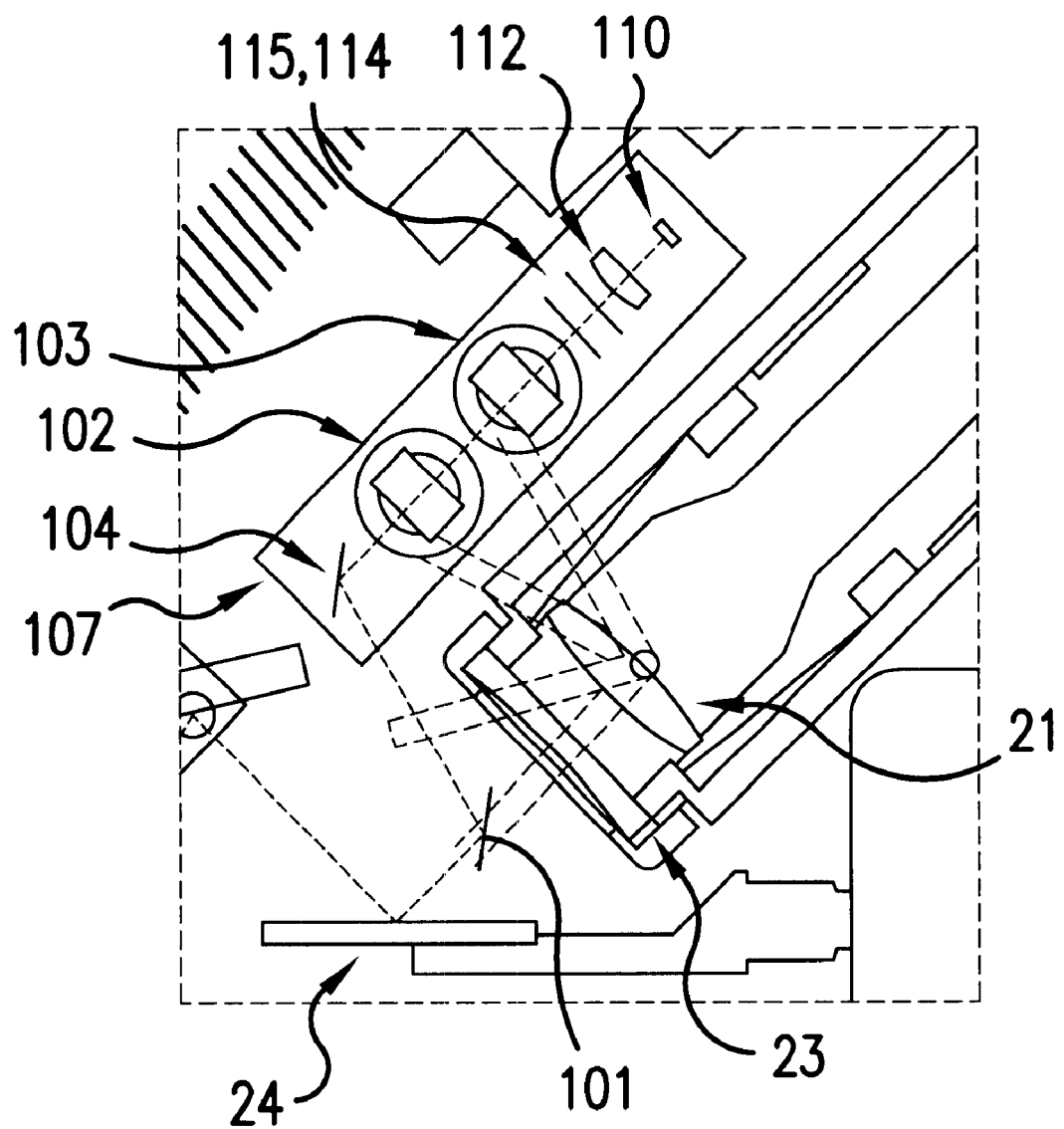
FIG. 4 shows the dashed area of FIG. 2, the detector means in more detail.

In FIG. 4, the part of the handpiece defined by the dashed line in FIG. 2 comprising the detector means is shown in greater detail. The detector means comprises a detector 110 and two light sources 102, 103 mounted in a holder for optical elements. The detector means further comprises an adjustable mirror 101. In sensing mode, the adjustable mirror 101 is positioned so as to transmit sensing light beams emitted from the light sources 102, 103 mounted in the optical holder 107 via the fixed mirror 104 to the first mirror 24, the second mirror 25, and the second focusing lens 30 which focuses the light beams on the target 40.

Likewise, the reflected sensing beams reflected from the target 40 are directed back to the detector means via the focusing lens 30 and the adjustable mirrors 24, 25. From the mirror 101 at the rotating arm 100 the reflected sensing beams are directed to the fixed mirror 104, where from they are directed towards the detector 110 for intensity detection.

Figure 5:
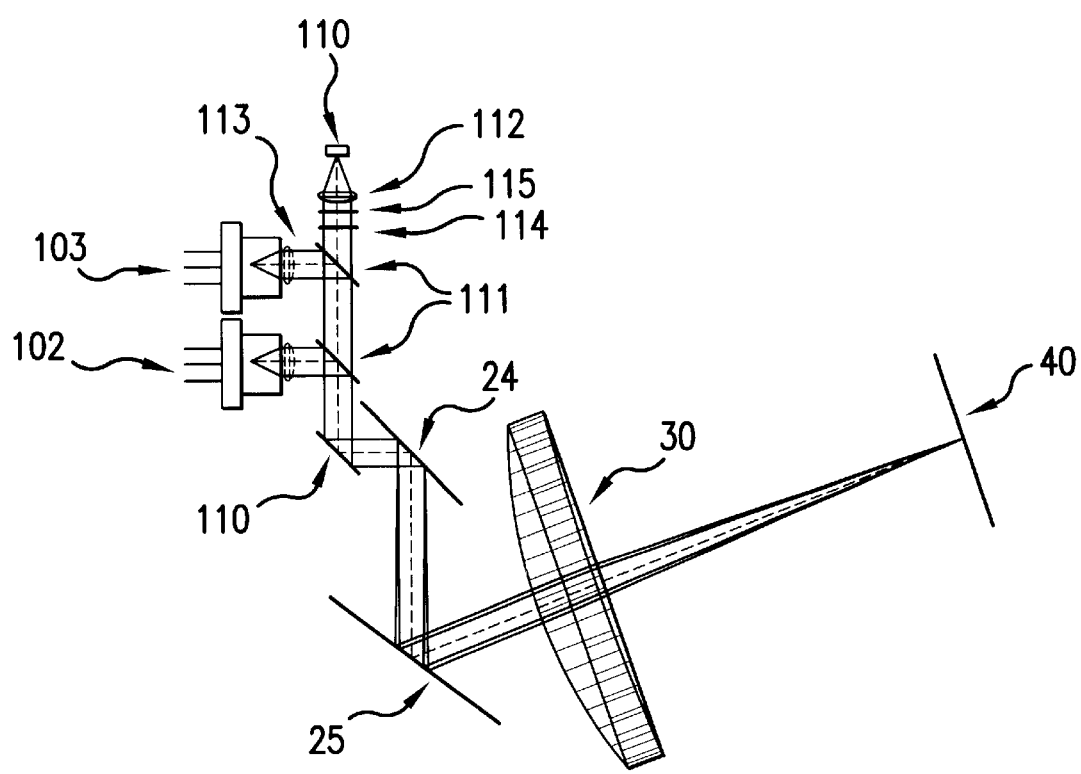
FIG. 5 shows detector means of the handpiece shown in FIG. 2 in sensing mode in greater detail.

In FIG. 5 the detector means are schematically shown in greater detail. For simplicity the mirror 104 is not shown in FIG. 5. The light sources 102, 103 are laser diodes which emit light at different wavelengths. Each of the emitted sensing light beams is collimated by respective collimating lenses 113 and is directed by beamsplitters 111 towards the adjustable mirror 101 and by the mirror 101, each of the sensing light beams is directed to the target 40 via mirror 24, mirror 25 and focusing lens 30. Thus, the output optics is used to scan both the sensing light beams and the light beams emitted from the beam-outlet end of the fibers. The sensing beams reflected from the target 40 propagate along the same path back to the beamsplitters 111. The polarisation of the light beams is changed when the light is reflected from the target 40, and since the transmittance of the beamsplitters 111 are dependent on the polarisation of the incident light beam the reflected sensing light beams reflected from the target 40 are transmitted through the beamsplitters, without reflection. A polarisation filter 114 and a blockout fitter 115 is positioned in front of the detector 110 to increase signal to noise ratio. A third focusing lens 112 focuses incident beams at the detector. To determine the color of tissue at the target 40 a red and a green light beam from respective light sources 102, 103 are alternately directed towards the target 40. The reflection of the red and the green light beams, respectively, from the target 40 are directed to the detector by the deflection means and are detected at the detector 110. The differences in the reflected light from light sources 102, 103 are calculated and tissue parameters, i.e. the color of the tissue, to be treated is thereby determined. Depending upon the tissue parameters to be determined, it is of course envisaged that the sensing beams may be visible light beams of any color, or it may be ultra violet light beams, or it may be infrared light beams.

As shown in FIG. 2, the optics and electronics of the handpiece 38 are protected by a plastic housing 36 provided in an ergonomical shape. An air tube 34 may be positioned on the handpiece 38 for providing suction of air from in front of the optics of the handpiece 38 in order to absorb any material ablated from the tissue of the object being treated with the apparatus of the present invention.

The light beams from the two glass fibers 6, 7 transmitted from the cable 1 through the optics of the handpiece and to the object, intersect at a distance equal to the focal length of the focusing lens 30, i.e. at the distance where the light from the $CO_2$ laser is focused. This is the distance at which the handpiece should be held from the object to obtain the best treatment result, and the intersection of the two visible light beams assists the operator in maintaining a correct distance to the tissue surface.

Because of the importance of keeping the $CO_2$ focal point on the tissue surface, the presently preferred embodiment of the handpiece 38 shown in FIG. 2 further comprises a magnetic distance member 33 connected to the handpiece 38 with fastening means 32. The fastening means may comprise a magnet whereby the distance member 33 is easy to connect to and disconnect from the handpiece 38.

The embodiment of the invention shown in FIGS. 1–5 may further comprise an infrared light detector for determination of the temperature of the target.

Furthermore, the arm 100 with mirror 101 may be replaced by a beamsplitter, whereby it will be possible to determine tissue parameters and treat the tissue simultaneously.

Figure 6:
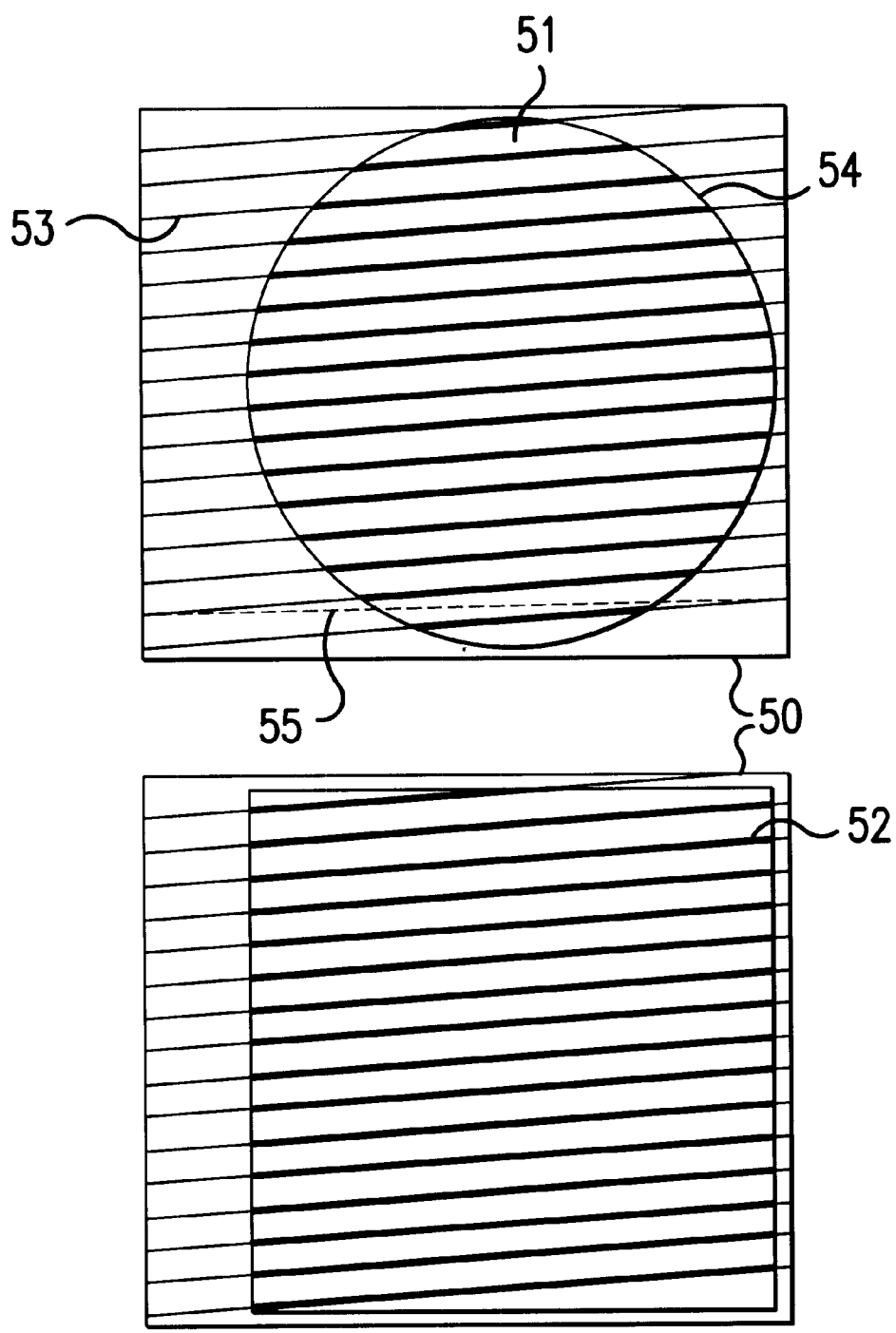
FIG. 6 shows a circular and a quadratic scan area.

In FIG. 6, a quadratic scan area 52 and a circular scan area 51 are shown. The actual laser scan area is indicated by reference numeral 50, but only the scan areas 51, 52 are used for tissue treatment. The thin lines 53 and the thick lines 54 indicate the path which the laser beam follows during a scan. The thin lines 53 indicate parts of the scan where the laser is turned off, while the thick lines 54 indicate parts of the scan where the laser is turned on.

The scan is performed as a slow forward/fast return-scan (a TV-scan, but without interlacing). The scan starts at the lower left corner of the actual scan area 50. The laser beam is moved towards the right, and when the laser beam enters the tissue treatment scan area 51 or 52, the laser is turned on. When the laser beam leaves the tissue treatment scan area 51 or 52, the laser is turned off, and when the laser beam reaches the right edge of the actual scan area 59, the beam is quickly retraced or moved to the left edge of the actual scan area 50, and a new scan line can be initiated.

In stead of turning the laser on and off, the speed of the movement of the laser beam may be increased to a speed sufficiently high for the laser beam not to ablate the tissue surface.

The fast movement (trace and retrace) of the laser beam between the right and left edges of the actual scan area 50, is accomplished by controlling the galvanometer 26. In order to let the mirror 24 settle after the fast movement from the right edge of the actual scan area 50 to the left edge, the first part of the scan line is not used for tissue treatment. The slower movement of the laser beam from the bottom to the top of the actual scan area 50 is accomplished by controlling the linear actuator 29 in a constant movement of the mirror 25.

A quadratic scan area of approx. 9*9 mm comprises 30 scan lines, and the max. scanning speed is app. 300 mm/s.

The operator of the apparatus controls the scanning using a pedal. When the pedal is activated, a scanning starts. After finishing the scanning, the $CO_2$ laser is turned off, and the visible light beam scans around at least a part of the circumference of the scan area 51 or 52 thereby indicating the size, shape and position of the scanned area 51 or 52. The operator may now move the handpiece and select a new scan area, e.g. a scan area abutting the area just scanned, and when the operator releases the pedal and again activates it, a new scanning will take place. In this way, the operator of the apparatus may easily scan larger areas of the tissue by scanning several neighbouring areas.

Figure 7:
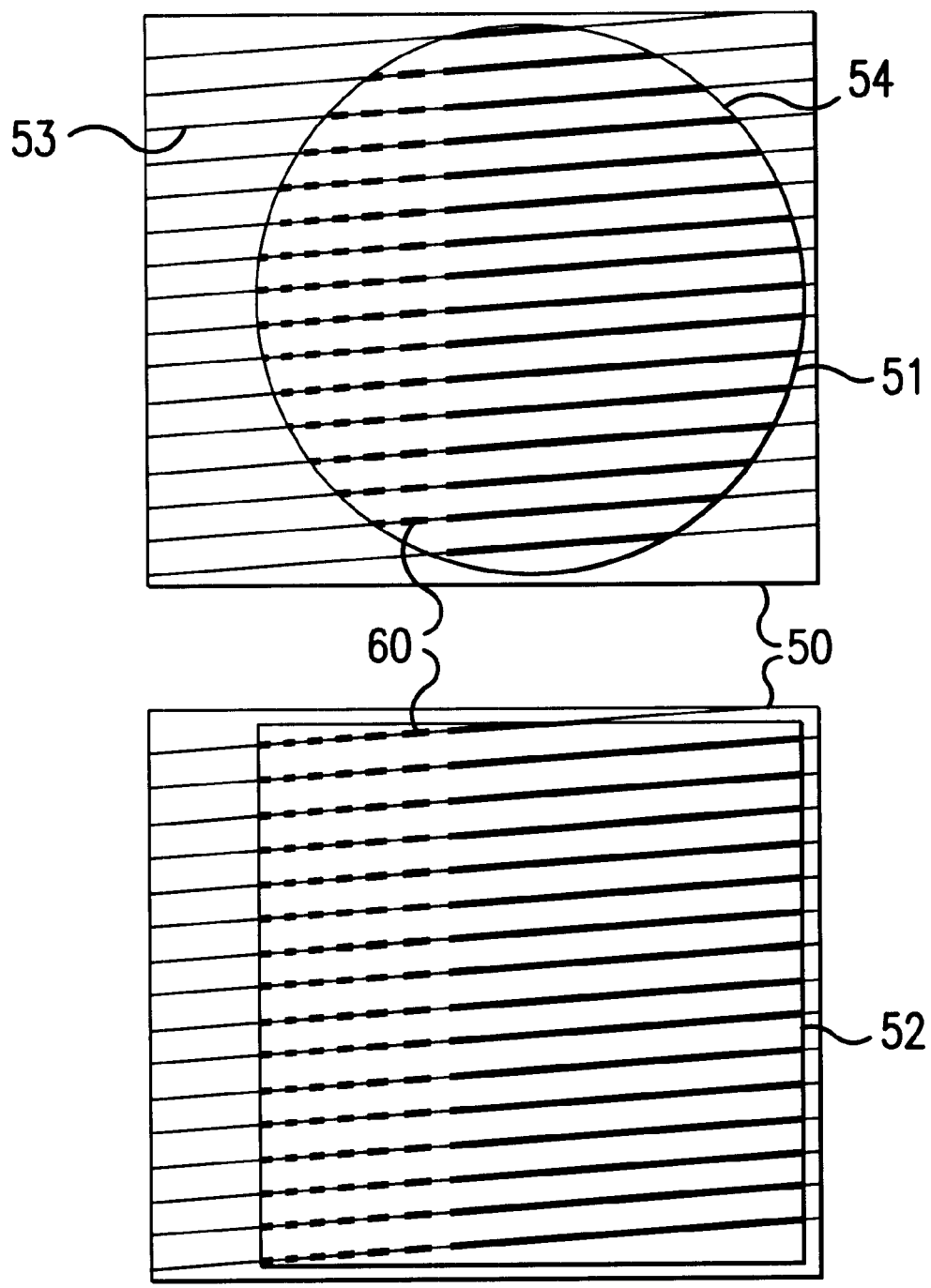
FIG. 7 shows a circular and a quadratic scan area with a single-sided fade-out scan pattern.

In FIG. 7, a quadratic scan area 52 and a circular scan area 51 with single-sided fade-out intensity scan lines 60 are shown. The fade-out intensity is accomplished by pulse modulating the laser power in shorter pulses as the intensity is faded out.

Figure 8:
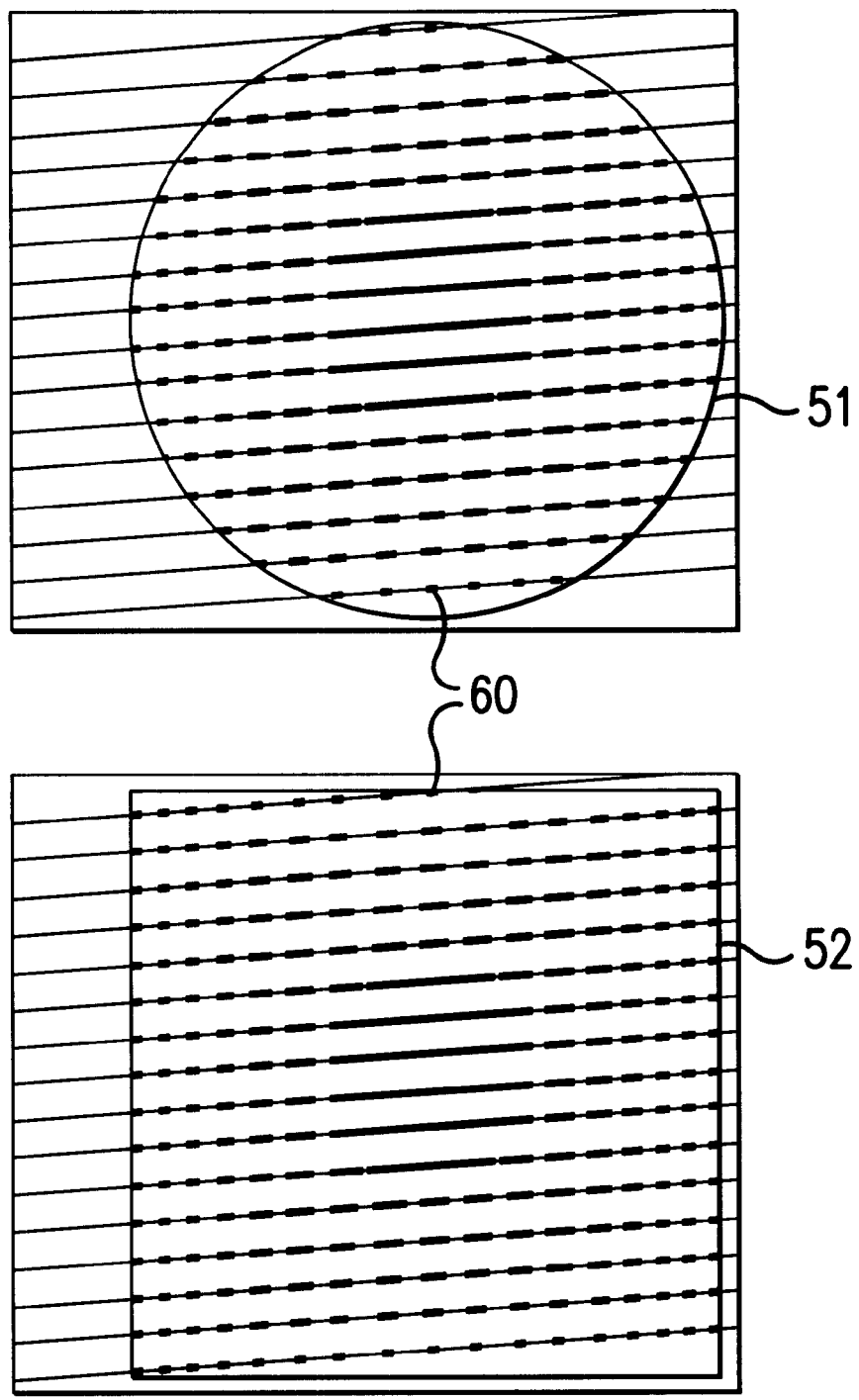
FIG. 8 shows a circular and a quadratic scan area with a four-sided fade-out scan pattern.

In FIG. 8, a quadratic scan area 52 and a circular scan area 51 with four-sided fade-out intensity scan lines 60 are shown.

The effect of using the fade-out intensity scan lines 60 is to create a smooth transition from a non-ablated area of the tissue to an ablated area.

The size and shape of the fade-in and fade-out scan areas may be selected using selectors on the handpiece 38.

It should be understood that a fade-in or a fade-out effect may be accomplished by gradually increasing or decreasing the intensity of the laser light, respectively, or by decreasing or increasing the speed of the movement of the laser beam, respectively.

Figure 9A:
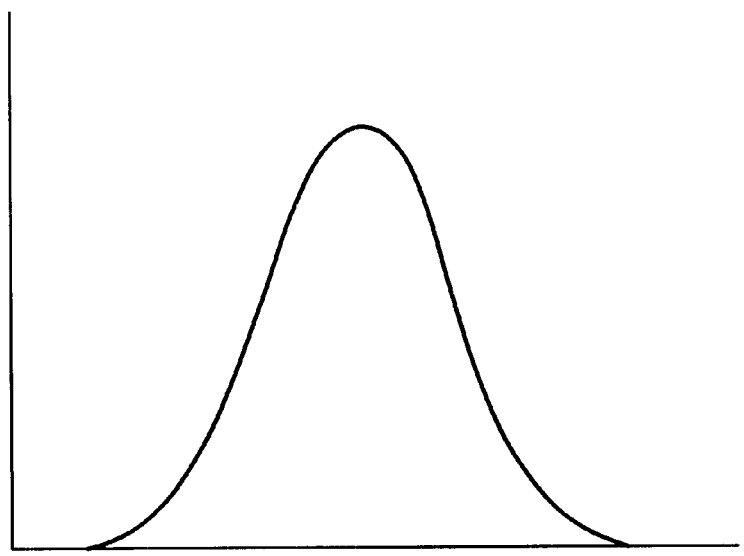
FIG. 9 shows a cross section of a standard laser beam and an example of a cross section of a laser beam more suitable for use in the handpiece of the present invention.

In FIG. 9a, the beam profile for a standard laser beam transmitted via mirrors and standard lenses is shown. The beam profile is Gaussian with a high light intensity in the center of the beam. Only the high intensity center of the beam can ablate the tissue.

Figure 9B:
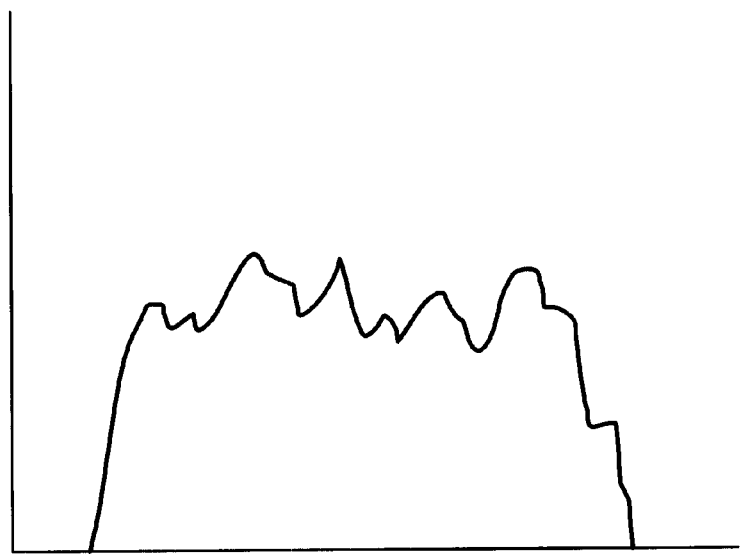

In FIG. 9b, a typical beam profile for a laser beam transmitted through the optical fiber 2 used in the apparatus according to the present invention is shown. The high intensity part of the beam profile is not limited to the center of the profile, but almost the complete beam profile has a sufficiently high intensity for ablating the tissue. When the laser light at 10.6 $\mu$m wavelength is transmitted through the 500 $\mu$m optical fiber 2, the laser light is changed from a single mode laser beam to a multi mode laser beam. A multi mode laser beam has a more uniform intensity profile compared to the single mode laser beam.

When using a Gaussian shaped beam, there is a risk of overexposing the tissue exposed by the center of the beam, while the parts of the tissue exposed by the edges of the beam are underexposed. This may result in thin lines of scars in the tissue. Using a non-Gaussian shaped beam, as the beam provided by the optical fiber used in the apparatus according to the present invention, the risk of making scars in the tissue is minimized.

One of the advantages of using a broadened light beam is, that the risk of drawing lines on the tissue as with the high intensity Gaussian beam is minimized.

Figure 10:
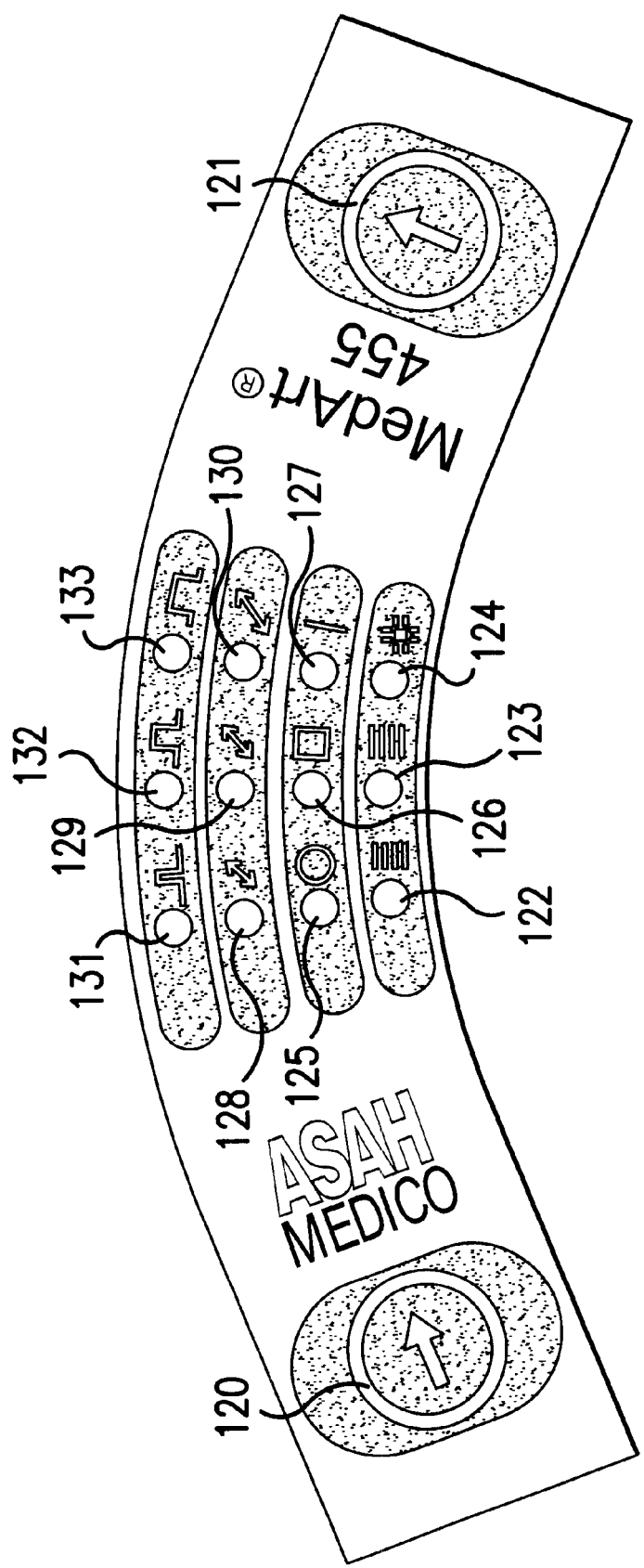
FIG. 10 shows an unfolded view of the user interface means provided at the handpiece.

In FIG. 10 the user interface means of the handpiece is shown unfolded. The user interface means comprise two push buttons 120, 121 and twelve light emitting diodes arranged in four rows, each row comprising three diodes.

Each row is used to indicate selection of a parameter value of a corresponding parameter type.

The row comprising diodes 122, 123, and 124 indicates selection of shape of the scan pattern. Diode 122 is turned on when a circular scan pattern is selected, diode 123 is turned on when a quadratic scan pattern is selected and diode 124 is turned on when a line scan pattern is selected.

The row comprising diodes 125, 126, and 127 indicates selection of fade-in and fade-out patterns. Diode 125 is turned on when a pattern with fade-in from the left is selected, diode 126 is turned on when a pattern with fade-in from the left and fade out to the right is selected, and diode 127 is turned on when a pattern with fade-in and fade-out, respectively, from both sides as well as from top and bottom of the scan pattern is selected.

The row comprising diodes 128, 129, and 130 indicates selection of the size of the scan pattern. The diode 128 is turned on when a small scan pattern is selected, diode 129 is turned on when a medium sized scan pattern is selected, and diode 130 is turned on when a large scan pattern is selected.

If the quadratic scan pattern is selected, the scan area may be approx. 9*9 mm, approx. 6*6 mm, such as 6.5–7 mm*6.5–7 mm, or approx. 3*3 mm, such as 3.5–4 mm*3.5–4 mm, if the scan pattern is circular, the diameter of the circle may be approx. 9 mm, such as 10 mm, approx. 6 mm, such as 6.5–7 mm, or approx. 3 mm, such as 3.5–4 mm, and if the scan pattern is a line, the length of the line may be approx. 9 mm, such as 10 mm, approx. 6 mm, such as 6.5–7 mm, or approx. 3 mm, such as 3.5–4 mm.

In the example above, the number of scan lines in a quadratic or circular scan may be approx. 10 scan lines per scan area if the scan size is small, or the number of scan lines may be approx. 20 scan lines per scan area if the scan size is medium, or the number of scan lines may be approx. 30 scan lines per scan area if the scan size is large.

Thus, the time to complete a scan depends on the scan size and the scan speed. If for example the scan speed is high the time to complete a scan is approx. 0.15 sec if the scan size is small, approx. 0.5 sec if the scan size is medium, and approx. 1 sec if the scan size is large. If the scan speed is medium the time to complete a scan is approx. 0.2 sec if the scan size is small, and approx. 0.7 sec if the scan size is medium, and approx. 1.5 sec if the scan size is large. If then the scan speed is slow the time to complete a scan is approx. 0.3 sec if the scan size is small, and approx. 0.9 sec if the scan size is medium, and approx. 2 sec if the scan size is large.

The row comprising diodes 131, 132, and 133 indicates scan velocity. Diode 131 is turned on when a high scan velocity is selected, diode 132 is turned on when a medium scan velocity is selected, and diode 133 is turned on when a low scan velocity is selected.

Depending on the application of the handpiece, the high velocity may be equal to 350 mm/s. At the high velocity approx. 5 j/cm$^2$ is supplied to the scanned area. The medium velocity may be equal to 225 mm/s at which velocity approx. 8 J/cm$^2$ is supplied to the scanned area. The low velocity may be equal to 175 mm/s at which velocity approx. 10 J/cm$^2$ is supplied to the scanned area.

When scanning on different types of tissue, it is preferred to adjust the scan speed of the light beam in stead of adjusting the output power of the light beam. When scanning on tissue with a low absorption of light, such as dry skin, it is preferred to generate a high power density on the tissue, and the scan speed mode should be set to low. When scanning on tissue with an average absorption of light, the scan speed mode should be set to medium, and when scanning on tissue with a high absorption of light, the high scan speed mode should be selected.

Depression of the push button 121 causes one of the light diodes to start flashing in one row indicating that parameter values of the type corresponding to that row can be selected. By depressing push button 121 once more, a light diode in another row will start flashing and thus, by repeatedly depressing push button 121, parameter values of each type indicated by the user interface means may be selected.

In the row in which a light diode is flashing, the desired parameter value may be selected by depressing the push button 120 until the diode indicating selection of the desired parameter value is flashing.

Thus, selection of scan area parameter values of the handpiece may be done immediately prior to scanning of the treatment area. Selection is very simple and does not require utilization of an external computer for programming of desired scan patterns.

The different scan pattern parameter values are stored in the memory of the handpiece. This provides an easy to learn and understand user interface requiring a minimum of teaching of the operator. Furthermore, the weight of the cables and thereby of the handpiece is reduced because there is no need for cables connecting the handpiece to an external controller. Further, by storing scan pattern parameters in the memory of the handpiece, costs for an expensive programming device is avoided. Other scan patterns than the ones described above may be downloaded to the memory of the handpiece through its computer interface. When the desired scan patterns have been downloaded, the computer interface can be disconnected from the scan pattern parameter value source and the handpiece will be ready for use.

All functions of the handpiece is controlled by the processor. The processor is interfaced with the laser unit, the light emitting diodes and the two push buttons of the user interface means.

Figure 11:
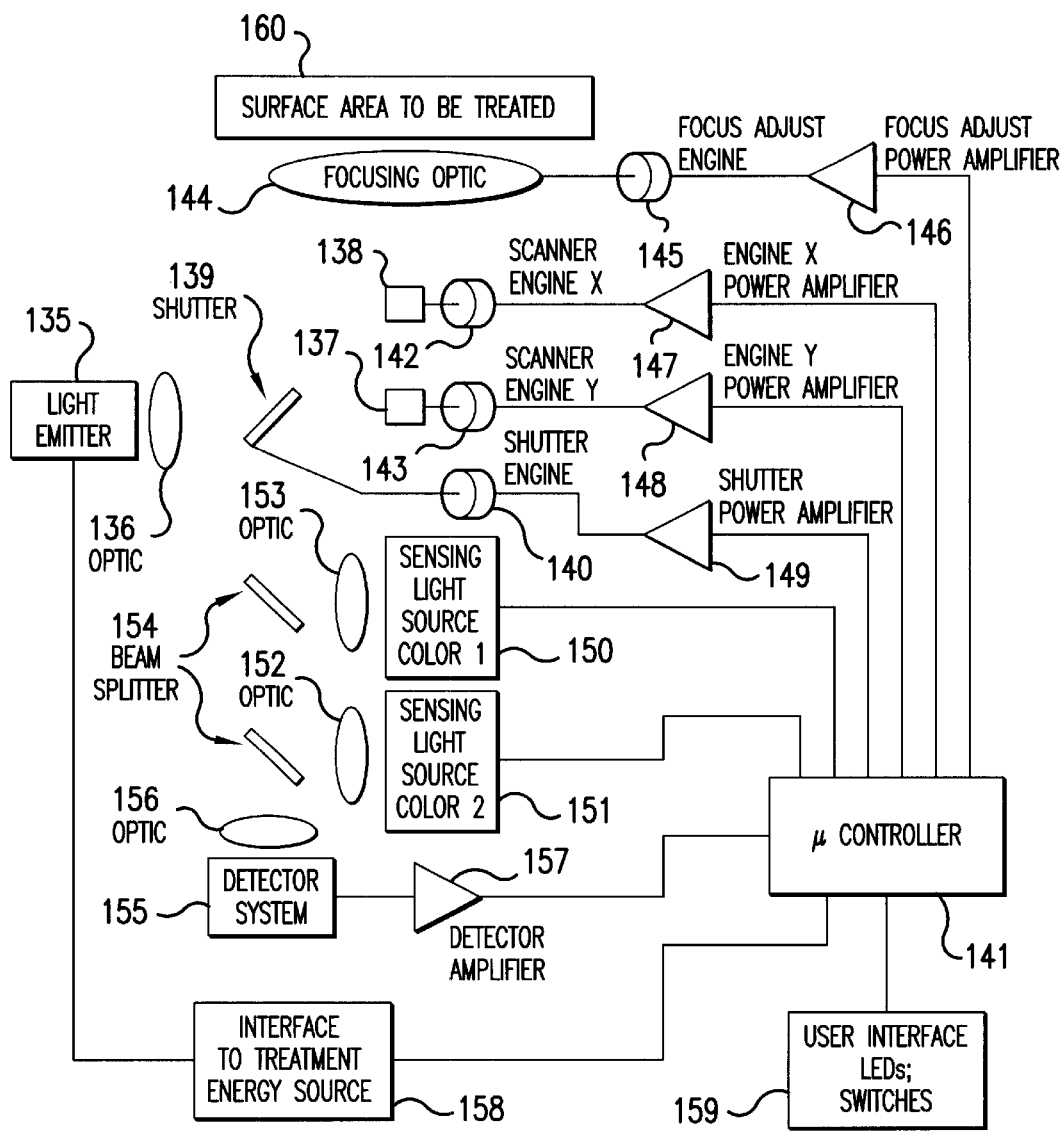
FIG. 11 shows a schematic diagram of the apparatus.

FIG. 11 shows a schematic diagram of the apparatus. A treatment light energy source 135 such as a light emitter, emits a first light beam (not shown). The first light beam is via optics 136 directed to adjustable mirrors 137, 138 whereby the first light beam is deflected towards the surface to be treated 160. The mirrors are controlled by scanner engine X 142 and scanner engine Y 143, respectively. Thus, the first deflection means comprises the adjustable mirrors 137, 138 and the scanner engines X and Y 142, 143. A shutter 139 is provided in the path of the first light beam to prevent the first light beam from being irradiated towards the surface to be treated 160. The shutter is controlled via shutter engine 140 by micro controller 141. To ensure focusing of the light beam at the surface area to be treated 160 adjustable focusing optic 144 is positioned in the path of the light beam. The focusing optic is adjusted via the focus adjust engine 145. Power amplifiers 146, 147, 148, 149 are provided for engines 145, 142, 143 and 140, respectively for amplification of the power signals. The micro controller 141 comprises the focus control means, the first deflection control means and the shutter control means.

Two light sources 150, 151 are provided for directing sensing light beams through optics 152, 153 and via beamsplitters 154 towards the surface area to be treated 160. A detector system 155 comprising the detector means detects the light reflected from the surface area 160 and directed to the detector system 155 via optic 156. The detected signals are transferred to the micro controller 141 via a detector amplifier 157. The micro controller 141 further comprises storage means for storage of coherent sets of signal values provided by the detector means at positions along a predetermined path and the respective corresponding positions, and first light beam control means for controlling parameters of the first light beam in response to the detected tissue parameters. Interface means 158 are provided to feedback parameters of the first light beam to the light emitter on the basis of the detected tissue parameters.

In an apparatus further comprising a detector array and array optics for forming an image of the target area, the micro controller 141 further comprises the image processing means for processing the output signals from the detector array.

In the apparatus shown schematically on the figure, the first and second deflection means and the first and second deflection control means are identical.

Further, user interface means 159 are provided comprising user interface, light emitting diodes, push buttons and switches.

Figure 12:
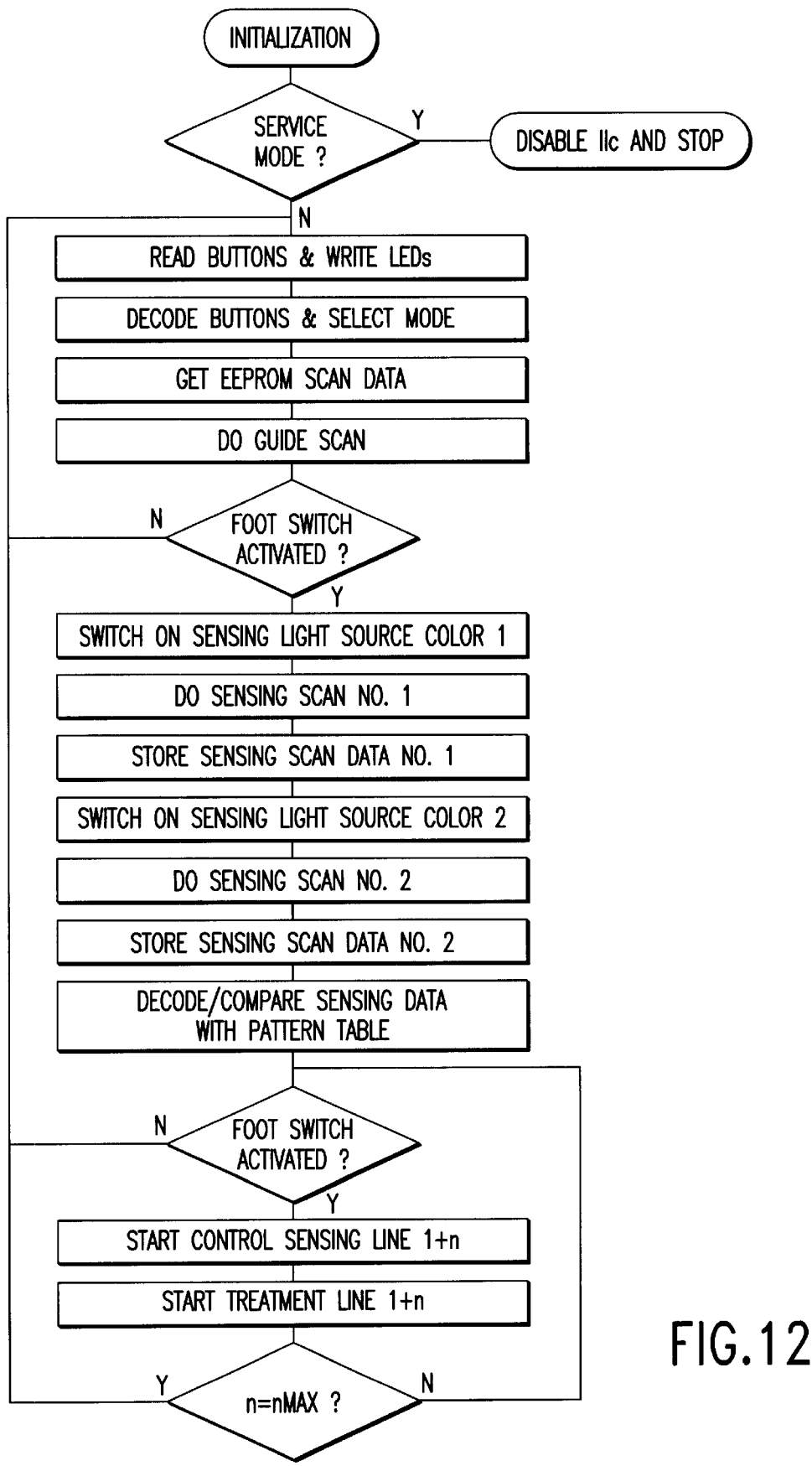
FIG. 12 shows a flow chart of the software controlling the scan parameters.

In FIG. 12 a flow chart illustrates processor operation before the treatment scan is started. In the illustrated processor operation two sensing light beams are used and the light reflected from each of these is detected. The scan is performed as a line by line scan.

Processor operation starts in step 165 where the processor is initialized. Hereafter in step 166, the processor checks if the handpiece is in a service mode; If so, the bus IIC, which reads and writes the outputs from the microprocessor is disabled in step 167. If not, in step 168 activation of the push buttons of the user interface means are detected and the light emitting diodes are turned on and off accordingly as previously described. In step 169, the parameter value selections are recorded and the corresponding scan pattern is selected. In step 170, the processor gets data from the EEPROM and perform a guide scan in step 171, i.e. the visible light beam traverses the circumference of the scan pattern or a part thereof as previously described. In step 172, the processor checks if the foot pedal is depressed or activated. If not activated, the process is repeated from step 168. If the foot pedal is activated then the first sensing light source 151 is switched on in step 173 and in step 174, the sensing light scans the area to be treated along a predetermined path. In step 175, the data collected during the sensing scan is stored. In step 176, the second sensing light beam is turned on and in step 177, a second sensing scan is performed. In step 178, the data collected during the second sensing scan is stored. In step 179, the stored sensing data are decoded and compared with a pattern table. In step 180, the processor checks if the foot pedal is depressed or activated. If not activated the process is repeated from step 168. If the foot pedal is activated then a control sensing can is initiated from line 1+n in step 181, and the treatment scan is initiated in step 182 at line 1+n, where n is an integer. In step 183, it is controlled whether n is equal to a predetermined n MAX. If not the process is repeated from step 180, if n=n MAX, a new scan may be initiated from step 168.

When the system is in service mode an external unit may take over the control of the handpiece from the handpiece processor by taking control of the serial IIC bus. The handpiece processor checks whether an external computer is connected to the bus and if so control of the bus is transferred to the external computer. This may be useful when testing and adjusting the handpiece and when reprogramming the scanner.

Figure 13:
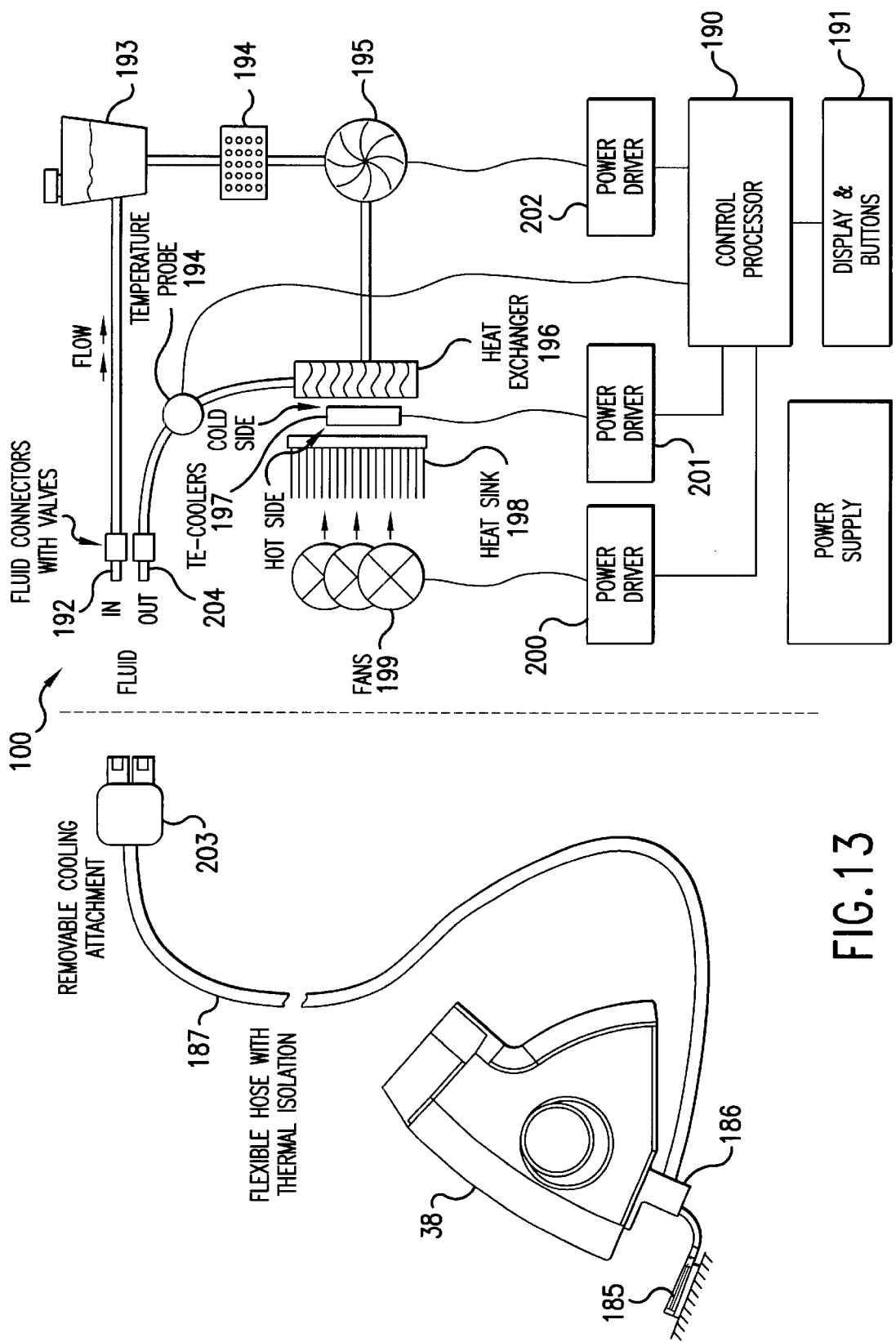
FIG. 13 shows a handpeice according to an embodiment of the present invention wherein a cooling member for cooling of the tissue to be treated is provided.

FIG. 13 shows a handpiece 38 according to an embodiment of the present invention wherein a cooling member 185 for cooling of the tissue to be treated is provided. The cooling member has an adapter for adapting the cooling member 185 to the handpiece. Further, a flexible hose 187 with thermal isolation is provided to connect the cooling member with a cooling system 188. A removable cooling attachment 203 is provided to the flexible hose 187 to easily connect and disconnect the cooling member 185 to the cooling system 188 via the flexible hose 187.

The cooling system 188 is connected to microprocessor 190, where from it is controlled. A user interface 191 is provided. The fluid coming from the cooling member via line 192 is directed to a cooling fluid reservoir 193 wherein also air is removed from the fluid. The fluid is via a particle filter 194 led to a fluid pump 195 controlled by microprocessor 190. The fluid pump 195 leads the fluid to a heat exchanger 196. TE coolers 197 are positioned next to the heat exchanger 196 and controlled by the microprocessor 190. A heat sink 198 and fans 199 for cooling the heat sink is provided. The fans 199 also being controlled by the microprocessor 190. Power drives 200, 201, 202 are provided for respectively, the fans 199, the TE-coolers 197 and the fluid pump 195. The fluid from the heat exchanger is led to an outlet 204 via the flexible hose 187, to be used in the cooling member 185.

Figure 14:
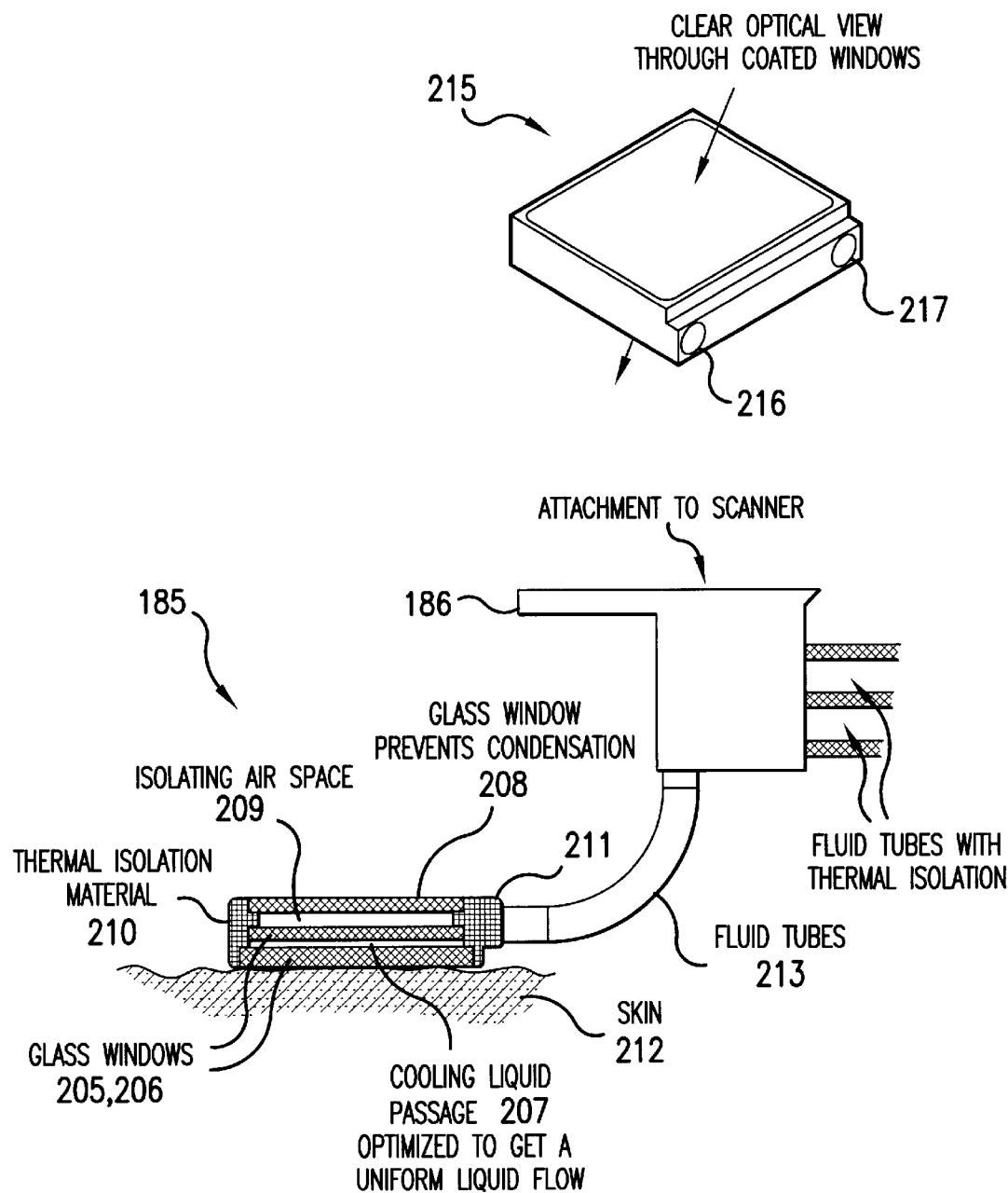
FIG. 14 shows the cooling member in more detail.

FIG. 14 shows the cooling member 185 in more detail. The cooling member 185 is positioned at the tissue to be treated 212. The upper and the lower glass window 205, 206, respectively, are positioned in a frame 210, 211 and connected so as to form a volume 207, wherein the fluid may flow. The volume 207 is optimized to get a uniform liquid flow. Above the upper and the lower glass windows 205, 206, a third glass window 208 is positioned in the frame 210, 211 so as to create an isolating air space 209 between the glass windows 205, 206 and the glass window 208. Hereby, the third glass window 208 prevents condensation. The frame 210, 211 comprises thermal isolation material for isolation purposes. A fluid tube 213 is connected to the adapter for attachment to a scanner, where from fluid tubes 214 leads to the cooling system. Also in FIG. 14 a top view 215 of the cooling member 185 is shown. An inlet 216 for insetting cooling fluid and an outlet 217 for outletting cooling fluid from the volume is provided at one side of the cooling member and the cooling member 185 is via coatings on the windows 205, 206 and 208 transparent to the light beams used during treatment.

What is claimed is:

1. A handpiece for an apparatus for tissue treatment, comprising:
    an output for emission of a first light beam towards a target area of tissue to be treated;
    a cooling member adapted to be positioned at the target area for cooling of tissue at the target area, said cooling member being at least partly transparent to the first light beam;
    an input adapted to receive a first beam-outlet end of a first optical fiber for alignment of the first optical fiber with an axis of the handpiece so that a first light beam emitted from the first beam-outlet end is transmitted substantially along the axis;
    an output for emission of the deflected first light beam towards the target area of tissue to be treated;
    detector means for detecting the type of tissue at the target area;
    first light beam control means for controlling parameters of the first light beam emitted towards the target area in response to the detected type of tissue, whereby various types of tissue can automatically be treated differently; and
    first movable deflection means for variable deflection of the first light beam emitted from the beam-outlet end, said first movable deflection means comprising a first mirror that is rotatable around a first axis.

2. The handpiece according to claim 1, said cooling member further comprising:
    a frame;
    an upper window positioned in the frame; and
    a lower window positioned in the frame, the frame, the upper window, and the lower window defining a volume therebetween for receiving and holding a cooling liquid.

3. The handpiece according to claim 2, said cooling member further comprising:
    an inlet for inputting cooling liquid to the volume; and
    an outlet for outputting cooling liquid from the volume.

4. The handpiece according to claim 1, wherein the detector means comprises light detectors for detection of intensity of light reflected from tissue at the target area.

5. The handpiece according to claim 1, wherein the detector means comprises infrared detectors for detection of temperature of tissue at the target area.

6. The handpiece according to claim 1, wherein the detector means comprises a detector array for detection of an image formed on the array.

7. The handpiece according to claim 6, further comprising image processing means for processing the image detected by the detector array.

8. The handpiece according to claim 7, wherein the imaging processing means is adapted to calculate the size of a spot of light illuminated by the first light beam.

9. The handpiece according to claim 8, further comprising:
    output optics for focusing the first light beam onto the surface of tissue to be treated and movably positioned at the output of the handpiece; and
    focus control means for adjusting the position of the output optics in response to the value of the calculated spot size.

10. The handpiece according to claim 1, wherein the first movable deflection means further comprises a second mirror that is rotatable around a second axis.

11. The handpiece according to claim 10, wherein the first axis is substantially perpendicular to the second axis.

12. The handpiece according to claim 9, further comprising first deflection control means for controlling the first movable deflection means in such a way that the first light beam is deflected along a predetermined path across the target area to be treated.

13. The handpiece according to claim 12, wherein the first deflection control means are adapted to control the first movable deflection means to deflect the first light beam to scan the target surface area line by line.

14. The handpiece according to claim 1, further comprising tissue type storage means for storage of coherent data sets of signal values provided by the detector means at predetermined positions along the predetermined path of the first light beam and the corresponding positions of the deflection means thereby mapping tissue parameters as a function of relative positions along the path in the storage.

15. The handpiece according to claim 14, wherein the first light beam control means is adapted to control at least one parameter of the first light beam during a second scan of the light beam along the predetermined path in accordance with the coherent data sets stored in the tissue type storage.

16. The handpiece according to claim 1, further comprising a first probing light source for illuminating tissue at the target area and wherein the detector means is adapted to detect light that is reflected from the illuminated tissue.

17. The handpiece according to claim 16, further comprising a second probing light source for illuminating tissue at the target area and wherein the first and second probing light sources emit light of different wavelengths.

18. The handpiece according to claim 17, wherein each of the first and second probing light sources comprises a light emitting diode.

19. The handpiece according to claim 18, wherein the first probing light source comprises a light emitting diode for emission of light in the wavelength range where the light is red.

20. The handpiece according to claim 18, wherein the second probing light source comprises a light emitting diode for emission of light in the wavelength range where the light is green.

21. The handpiece according to claim 16, wherein the type of tissue is characterized by the intensity of the light that is reflected from the illuminated tissue.

22. The handpiece according to claim 1, further comprising user interface means for selection of parameters of the handpiece.

23. The handpiece according to claim 22, wherein the parameters comprise a scan velocity.

24. The handpiece according to claim 22, wherein the parameters comprise a first light beam intensity.

25. The handpiece according to claim 22, wherein the parameters comprise a size of the target surface area.

26. The handpiece according to claim 22, wherein the parameters comprise a shape of the target surface area.

27. The handpiece according to claim 1, wherein
the input is further adapted to receive a second beam-outlet end of a second optical fiber for transmission of a visible second light beam to the handpiece and for alignment of the second optical fiber with the axis of the handpiece so that the visible second light beam emitted from the second beam-outlet end is transmitted substantially in parallel with the axis, and further comprising
second movable deflection means for variable deflection of the visible second light beam in such a way that the first and the second light beams emitted from the output of the handpiece illuminate substantially the same area of a target surface.

28. The handpiece according to claim 27, wherein the first and the second movable deflection means are identical.

29. The handpiece according to claim 27, further comprising second deflection control means for controlling the second movable deflection means and being adapted to control the second movable deflection means in such a way that the visible second light beam is scanned around at least a part of a circumference of the target surface area thereby indicating the size, shape and position of the target surface area.

30. The handpiece according to claim 29, wherein the shape of the target surface area is polygonal and the second deflection control means is further adapted to control the second moving means in such a way that the visible second light beam is scanned along one edge of the polygon.

31. The handpiece according to claim 1, further comprising a distance member connected to the handpiece at the output with fastening means and for indicating the desired distance between the patient and the output.

32. The handpiece according to claim 31, wherein the fastening means comprises a magnet so that the distance member can easily be disconnected from the handpiece.

* * * * *

UNITED STATES PATENT AND TRADEMARK OFFICE
CERTIFICATE OF CORRECTION

PATENT NO.    : 6,383,177 B1  Page 1 of 1
DATED         : May 7, 2002
INVENTOR(S)   : Olav Balle-Petersen et al.

It is certified that error appears in the above-identified patent and that said Letters Patent is hereby corrected as shown below:

<u>Title page,</u>
Item [75], Inventors:, change "Olav Balle-Petersen, Humlebaek; Bjarne Asah, Taastrup; Casper Dolleris, Frederiksberg, all of (DK)" to -- Olav Balle-Petersen, Humlebaek; Bjarne Asah, Taastrup, both of (DK); Casper Dolleris, Vancouver (CA) --.

Signed and Sealed this

Eighteenth Day of March, 2003

JAMES E. ROGAN
*Director of the United States Patent and Trademark Office*